(12) United States Patent
Anderson et al.

(10) Patent No.: US 8,336,542 B2
(45) Date of Patent: Dec. 25, 2012

(54) FAULT INDICATOR

(75) Inventors: Gregor John McLennan Anderson, Ware (GB); Stephen James Harvey, Ware (GB); Andrew Roderick Taylor, Ware (GB); Daniel Thomas De Sausmarez Lintell, Warwick (GB); Mark Digby Teucher, Somerset (GB); James Anthony West, Somerset (GB)

(73) Assignee: Glaxo Group Limited, Greenford, Middlesex (GB)

( * ) Notice: Subject to any disclaimer, the term of this patent is extended or adjusted under 35 U.S.C. 154(b) by 955 days.

(21) Appl. No.: 11/913,945

(22) PCT Filed: May 12, 2006

(86) PCT No.: PCT/GB2006/001757
§ 371 (c)(1),
(2), (4) Date: Jul. 10, 2008

(87) PCT Pub. No.: WO2006/123110
PCT Pub. Date: Nov. 23, 2006

(65) Prior Publication Data
US 2009/0078252 A1      Mar. 26, 2009

(30) Foreign Application Priority Data

May 16, 2005   (GB) .................................. 0509952.8

(51) Int. Cl.
*A61M 16/00*    (2006.01)
*A62B 9/00*     (2006.01)
*A62B 27/00*    (2006.01)
*G08B 3/00*     (2006.01)
*G08B 5/00*     (2006.01)

(52) U.S. Cl. .......... 128/202.22; 128/203.15; 128/203.21
(58) Field of Classification Search ............. 128/202.22, 128/203.12, 203.15, 203.21
See application file for complete search history.

(56) References Cited

U.S. PATENT DOCUMENTS

| 3,759,095 | A | * | 9/1973 | Short et al. ...................... 73/157 |
| 4,224,824 | A | * | 9/1980 | Giusti ............................. 73/159 |
| 5,447,151 | A | * | 9/1995 | Bruna et al. ............. 128/203.15 |
| 5,582,162 | A | | 12/1996 | Petersson |
| 5,590,645 | A | | 1/1997 | Davies et al. |
| 2003/0172927 | A1 | | 9/2003 | Young et al. |

FOREIGN PATENT DOCUMENTS

| EP | 1522325 B1 | 4/2005 |
| JP | 56-112170 U | 1/1981 |
| JP | 59-064477 | 4/1984 |
| JP | 2004512147 A | 4/2004 |
| WO | 02/36189 A1 | 5/2002 |
| WO | 03/061743 A | 7/2003 |
| WO | 2005/014089 A1 | 2/2005 |

* cited by examiner

*Primary Examiner* — Loan Thanh
*Assistant Examiner* — Kathryn D. Sheikh
(74) *Attorney, Agent, or Firm* — Robert J. Smith

(57) ABSTRACT

A fault indicator for a strip advancement mechanism comprising a base that defines a fault sensing portion of a path for at least a component of a strip, an element for bearing against a strip, or a component of the strip, while it passes through the fault sensing portion of the path, wherein the element is adapted to move from that bearing or non-fault position, to a fault indicating position in the event of the strip or the component of the strip ceasing to pass through the fault sensing portion of the path.

15 Claims, 33 Drawing Sheets

FAULT INDICATOR

CROSS-REFERENCE TO RELATED APPLICATIONS

This application is filed pursuant to 35 USC 371 as a United States National Phase Application of International Patent Application Serial No. PCT/GB2006/001757 filed on 12 May 2006, which claims priority from GB 0509952.8 filed on 16 May 2005 in the United Kingdom.

RELATED APPLICATION

The present application claims priority from UK patent application No. 0 509 952.8 filed on 16 May 2005, the entire content of which is hereby incorporated herein by reference.

FIELD OF THE INVENTION

The present invention relates to a fault indicator for use in a device comprising a strip advancement mechanism. In particular, the fault indicator can be used in an inhaler comprising a strip having a releasable product thereon or therein, such as a dry powder medicament. The medicament may be, for example, for treatment of bronchial, tracheal or lung disorders, such as asthma. Medicaments for treatment of other disorders may also be dispensed by such inhalers.

BACKGROUND TO THE INVENTION

Devices containing strip advancement mechanisms for feeding strips containing medicaments are well known. Such devices can advance strips containing medicaments in blisters, or in other forms of pocket, in the strip, in a stepwise manner, past or to a mouthpiece provided on the device or inhaler so that the medicament can be inhaled through the mouthpiece. The medicament may be in a dry powder form. Such inhalers include the DISKUS® inhaler manufactured by GlaxoSmitKline, and those disclosed in U.S. Pat. No. 5,590,645, PCT Patent Application No. WO 03/061743 and US Patent Application No. US2003/0172927. The entire disclosures of each of the above publications are incorporated herein by way of reference.

Prior art inhaler devices generally feed either one or, in the case of WO 03/061743, two strips of medicament from one or two source spools within the device to or past a mouthpiece of the inhaler device. The feeding of the strip is achieved by a strip feeding mechanism that usually comprises a series of gears and/or spools within the device. The mechanism guides the strip and lead spools are provided for winding up the spent strip components.

The devices usually release the medicament from the strip at or adjacent to a mouthpiece by opening the blisters in the strip, for example by piercing, tearing or rupturing the strip, or by peeling a top layer from a bottom layer of the strip. Other forms of strip manipulation might also be used. The released medicament can then be administered by the patient by inhalation through the mouthpiece.

Generally, each blister or pocket, for example between two layers, defines or encapsulates a predetermined or pre-metered dose of medicament. Further, the top layer is usually a metal based foil cover sheet for peeling off a metal based foil base sheet having blister pockets therein. In particular, the foil will usually be a laminated metal and plastics sheet.

As previously indicated, the devices of the prior art generally rely upon one or more lead spool to wind up spent strip components. This winding action pulls unspent strip from the source spool and through the device. Some devices, however, also link the gears or spools of the strip advancement mechanism (but usually not the source spool) together so that the strip can be supported around a tortuous passage through the device. Preferably this involves rotating, driven, strip followers at each bend. They provide support for the strip for helping the strip to entrain around its path within the device.

If the strip (or one of the components) breaks or otherwise fails, e.g. by stretching, delaminating or tearing, in one of these devices, its pull-through mechanism, such as one relying upon one or more lead spool for winding up spent strip components, may no longer be able to pull the strip through the device correctly. For example, if a foil cover sheet tears, further dispensing of medicament may not be possible despite the strip continuing to be fed by the pulling of the base sheet through the device since further parts of the cover sheet might then not be peeled off the base sheet. A user, however, would not necessarily notice if the device had stopped working properly since the feed mechanism would still feel like it is functioning properly. Therefore, in the case of a failure of the peeling mechanism, there is a risk that a user might continue to use the inhaler in the false belief that it was still administering medicament, thereby under-dosing himself.

Another form of failure can occur. The cover sheet usually has a loop at its free end. That loop usually is fitted over a post on its lead spool, perhaps through a slot in the post. However, if that loop, or the post, was to fail, then further winding up of the cover sheet may not be possible. That would then prevent the cover sheet from being correctly peeled away from the base sheet. This also is undesirable.

It would therefore be desirable to provide a device that addresses, or provides an indication of, any one or more of the above potential problems.

SUMMARY OF THE INVENTION

The present invention provides a fault indicator for a strip advancement mechanism, the fault indicator comprising a base that defines a fault sensing portion of a path for at least a component of a strip, an element, optionally associated with the base, for bearing against a strip, or a component of the strip, while it passes through the fault sensing portion of the path, and wherein the element is biased to move from that bearing or non-fault position, to a fault indicating position in the event of the strip or the component of the strip ceasing to pass through the fault sensing portion of the path. The strip, or the component thereof, would cease to pass through the fault sensing portion of the path if the strip, or the component thereof, was to break or tear. Upon breaking, tearing, stretching or failing, either the strip would lose its tension, and therefore slacken, or a gap in the strip resulting from the breakage or tear would eventually pass the fault sensing portion of the path, i.e. upon one or more further activation of the strip advancement mechanism. As a result of the strip breaking, tearing, stretching or failing, therefore, the bias of the element would cause the element to move into its fault indicating position either immediately or upon one or more further activation of the strip advancement mechanism.

Preferably, the fault indicator provides a visual indication of a fault. The visual indication may be provided by a visual indicator attached to the element or to the base, such as a brightly coloured indicia or marker. Preferably the indicia or marker is red.

Preferably the visual indicator is hidden from view when the element is in a non-fault position and becomes visible upon the fault indicator moving into its fault indicating position. Alternatively, the fault indicator covers a visual indicator when the element is in a non-fault position and uncovers the visual indicator upon the fault indicator moving into its fault indicating position.

Preferably, the fault indicator comprises a tactile indicator, and/or an audible indicator. Preferably the tactile indicator is provided by a strip advancement resisting means, such as a toothed element or ratchet arm for bearing against a component of the strip advancement mechanism when the fault indicator is in the fault indicating position. Preferably it is a toothed element that bears against, or engages teeth of, a gear of the strip advancement mechanism. Then, any attempt further to advance the strip will cause the gears of the strip advancement mechanism to ratchet over the toothed element of the strip advancement resisting means, thereby providing a tactile feedback to the user. This ratcheting would also potentially provide an audible indicator.

Preferably the toothed element meshes onto the teeth by no more than half the tooth depth, or by 1 mm, to allow the ratcheting function to occur, rather than providing a blocking function—the fault indicator, however, may comprise a strip advancement lock-out mechanism. Preferably the strip advancement lock-out mechanism comprises a blocking means that, upon the fault indicator moving into the fault indicating position, blocks further actuation of the strip advancement mechanism. The blocking means may, like the tactile indicator, preferably comprises a toothed element for bearing against a gear of the strip advancement mechanism. The toothed element may simply be forced against the teeth with a more substantial force than in the tactile indicator, thereby causing the blocking of the gear. Preferably, however, the toothed element meshes by more than half the depth of the teeth, and more preferably by more than 75% of the depth of the teeth.

The blocking means, the visual indicator, the audible indicator or the tactile indicator may involve a two or more part activation sequence. For example, upon the fault indicator moving into the fault indicating position, the blocking means, the visual indicator, the tactile indicator, or a component associated therewith, may be advanced into a first position, and then upon one or more further activation of the strip advancement mechanism, a further element, for example a trigger of the strip advancement mechanism, may then be brought into engagement with the blocking means, the visual indicator, the tactile indicator, the audible indicator, the blocking indicator or a component associated therewith.

Preferably, the element is biased by a spring for biasing the fault indicator into the fault indicating position. Preferably the spring is in the form of a resilient member extending away from the element. Preferably it is integrally formed with the element. The element may alternatively itself be a resilient member, biased by tension in the strip into a non-fault position, and released to a fault indicating position upon the strip breaking, tearing, stretching or failing. For example, the element may be a resilient post or arm that extends either perpendicular or parallel to the direction of travel of the strip or component thereof when in the non-fault position, but in another direction when in the fault indicating position.

Preferably the fault indicating position is reached by movement of the element from its non fault position through the plane of the fault sensing portion of the path for the strip. The fault indicating position might otherwise be reached by movement of the element parallel to the plane of fault sensing portion of the path for the strip. In another embodiment, the fault indicating position is reached by movement of the fault indicator both through the plane and parallel to the plane. This may be in a two or more step motion. The motion may consist of a diagonal motion. Preferably, however, the element arrives at the fault indicating position in a one step motion e.g. by moving either through, across or diagonally across the plane, or by rotating relative to the plane, either through it or parallel to it.

The fault indicator may comprise two or more biased elements, such as those previously described, each being adapted to bear against different parts of the strip. This allows faults to be indicated in places that might otherwise not be detected.

Preferably the or each element bears against the strip, or the component thereof, towards the lead spool end of the path for the strip.

The present invention also provides a fault indicator for a strip advancement mechanism, the fault indicator comprising a base that defines a fault sensing portion of a path for at least a component of a strip, an element associated with the base for bearing against a strip, or a component of the strip, while it passes through the fault sensing portion of the path, and the element comprising a free spinning element about part of which a strip, or a component thereof, normally wraps in use, the element having a top surface having, or through which is visible, a visible indicia, wherein the indicia has no more than three degrees of rotational symmetry. By means of the indicia, rotation of the element can be verified by casual visual observation.

Preferably the indicia has no degrees of rotational symmetry. However, it may have one, two or three degrees of rotational symmetry, as may be appropriate, for allowing rotation of the element to be visually verified by casual visual observation, given the size of the element—a big element could have three degrees of rotational symmetry, whereas a small element might only be able to carry an indicia having one or no degrees of rotational symmetry. Otherwise it could become too cluttered for the rotation of the element to be verified by casual visual observation.

It is appreciated that prior art strip advancement mechanisms in inhalers comprise elements with top surfaces. However, indicia have not previously been provided for the elements specifically for allowing rotation verification of the elements to be carried out by visual inspection. Further, the mechanisms are covered by a non-transparent case, thereby not being visible in use. It is also pointed out that, although surface shapes such as crosses and circles for the spindles of such elements have existed, these have had four or more degrees of rotational symmetry. A cross has four degrees of rotational symmetry. A circle has an infinite number of degrees of rotational symmetry.

The indicia may be a brightly coloured marker on a neutral or white background.

The present invention also provides a method of verifying the correct functioning of a strip advancement mechanism, comprising providing on a rotating element a distinct marker suitable for visual inspection, and monitoring the marker to check for rotation of the element as the strip advancement mechanism is operated. Preferably the marker comprises an indicia as described above.

The strip advancement mechanism may be fitted in an inhaler. The inhaler may comprise a strip containing a medicament, the strip being advanced through the inhaler by the strip advancement mechanism.

Preferably a nose portion, or beak, is formed in the base of the fault indicator, around which nose portion, the path for the strip, or a component thereof, in use, will pass. The nose portion is used to help release the product or medicament from the strip. This may be by guiding and peeling a first layer or component of the strip, e.g. a cover sheet component, back and away from a second layer or component of the strip, e.g.

a base sheet. This peeling action will release a product or medicament that was encapsulated between the two layers, perhaps from within a previously sealed blister.

If provided, the free rotating element may form the tip of the beak or nose portion. Preferably, the rotating element then has a diameter of 5 mm or less. This provides an effective beak for sharply peeling back the cover sheet.

Preferably the nose portion, or beak, defines a portion of the path that lies upstream of the fault sensing portion of the path, i.e. closer to the source spool along the path than the fault sensing portion of the path. Then, fault sensing will occur after the cover sheet has been subjected to the peeling forces, or the forces of bending the foil cover sheet around the tight bend of the nose. This is advantageous since the strip, although generally able to withstand such bending forces, is more likely to break at that location, or at a location soon after that location, than at any other position along the strip's path. Positioning the nose portion upstream, therefore, increases the likelihood of the fault being sensed by the fault indicator.

Preferably, the strip comprises a cover sheet and a base sheet. Preferably the two sheets are coterminous along their edges. Preferably a medicament, or some other product, is encapsulated between the two sheets. If, in use, the strip is split for releasing the medicament, e.g. by peeling apart the two sheets, and if this occurs at a position along the path prior to the fault sensing portion of the path, then just the cover sheet, or just the base sheet, may extend through the fault sensing portion of the path.

Preferably the element bears against the cover of the strip. Alternatively, the element bears against the back of the strip. Other configurations, however, can have the element bearing against an edge or a side of the strip. It is also envisaged that the strip could have a non-rectangular or non-flat cross-section, Preferably a medicament is contained in a pocket between the base sheet and cover sheet. Preferably the pocket is a blister. The strip may contain additional layers.

The present invention also provides a strip advancement mechanism and a fault indicator therefor provided on a guide surface for the strip or the component thereof. Alternatively, the fault indicator may be as described above. The fault indicator, however, preferably comprises a brightly coloured indicator or indicia on a guide surface for the strip or the component thereof. In normal use, since it is on a guide surface for the strip, or the component thereof, the indicia would be covered by the strip, or the component thereof, and therefore will not be visible. However, upon tearing or breaking the strip, or the component thereof, and upon further winding the lead spool, the strip or the component thereof would be wound away from the indicia, thereby ceasing to cover the indicia to indicate a fault.

Preferably, the strip advancement mechanism defines additional portions of the path for the strip and has a strip entrained through or around it, with a length of the strip extending through the fault sensing portion of the path for the strip, and bearing against the element of the fault indicator or the fault indicator provided on the guide surface.

More than one fault indicator as previously described may be provided.

More than one strip may be provided. This would be beneficial for administering, for example, two-part compositions or medicaments.

The or each fault indicator may comprise two or more elements for bearing against the or each strip in more than one location or two or more fault indicators on the guide surfaces.

Preferably, however, each strip is provided with a single fault indicator of the present invention. Then, if either strip fails, a fault is indicated.

The present invention also provides a device comprising a strip advancement mechanism and a fault indicator as described above. Preferably the device is an inhaler for dispensing medicament. Preferably it is provided with a mouthpiece. Preferably the device contains a dry powder medicament encapsulated in a strip.

Instead of the above described element, the element may be the rotating element, and it may be visible through a window provided in an outer casing of the device. Preferably, in use the rotating element rotates with a strip as the strip passes through the fault sensing portion of its path due to the rotating element bearing against the strip. However, if the strip, or the component thereof, was to slacken, break, tear, stretch or fail, the strip will no longer bear against the rotating element, or it will not move, thereby not rotating the element. This non-rotation would be visible to the user through the window thereby alerting the user to the existence of the fault.

In another embodiment, the device simply has a window through which advancement of the strip can be viewed. The window may alternatively allow a different fault indicator to be viewed, such as a biased fault indicator as described above. Alternatively, the fault indicator may be a marking on a component of the strip advancement mechanism, such as a guide surface for the strip, or component thereof, and described above. Preferably, the guide surface is positioned on, or downstream of, a nose portion or beak of the device, i.e. nearer the lead spool than the nose portion.

The strip may be provided with indicia to assist in determining whether it is being advanced, e.g. a coloured line, preferably red.

The window may be in the form of a transparent, i.e. clear, trigger or a transparent groove follower thereof. A lead spool for winding up the strip, or a component thereof, may be visible through the trigger or groove follower, for visual inspection of the functionality inside the device.

The present invention also provides an inhaler comprising a mouthpiece, a medicament strip and a strip advancement mechanism, the strip advancement mechanism allowing medicament to be released from the medicament strip as it passes near the mouthpiece so that the medicament can be inhaled through the mouthpiece, the device comprising a light emitter and a light detector, the light emitter arranged to emit light across a lumen of the mouthpiece to the detector, and the detector being connected to a means for indicating a fault. Preferably the light is infrared light.

With this inhaler, when a user is inhaling, if medicament passes through the beam of light, then the inhaler is operating correctly and no fault will be indicated. However, if the beam is not broken or otherwise interfered with by the medicament when the patient inhales, then a signal can be transmitted by the detector to the means for indicating a fault to indicate that there is a fault to the patient. Preferably the detector is connected to an LED for emitting a visual indication of the fault. Preferably the visual indication is a red light. The indication, however, may be a buzzer.

The present invention also provides a strip advancement mechanism comprising a whistle hole provided in a guide surface for the strip, or a component thereof. The whistle hole is an audible fault indicator. In use, air currents in the device can be forced to pass the whistle hole, for example by ducting within the assembly. However, in normal use, the strip, or the component thereof, would cover the whistle hole so that it will not whistle. However, if the strip slackens, breaks, tears, stretches or fails, and therefore no longer covers the whistle hole, then the whistle hole would whistle due to the air currents.

Preferably this strip advancement mechanism is fitted into an inhaler, with the whistle hole is fitted near a mouthpiece of the inhaler. Then, the airflow in the device would be caused by inhalation by a patient through the mouthpiece. That airflow would then cause the whistle hole to whistle if a fault develops in the inhaler's medicament strip, which fault would uncover the whistle hole.

Preferably the whistle hole is provided on a nose portion or beak provided for the strip within the device, about which the cover strip passes in use.

Preferably a mouthpiece is provided for the device adjacent to a location in the device at which medicament will be dispensed from the strip. Preferably the fault indicator is also positioned adjacent to that dispensing location.

Preferably, whereas a cover sheet of the strip passes around a nose portion or beak, the base sheet of the strip passes onwards from the nose portion, after the cover sheet has been peeled off it, substantially without bending. Medicament thereon can then be inhaled off the base sheet of the strip, through the mouthpiece, which is positioned just past the nose portion, or beak, as well.

Preferably the element for bearing against the strip, or the component thereof, is provided just for bearing against the cover sheet component of the strip.

The device may comprise two or more source spools so that two or more strips can be fed through the device. A fault indicator may be provided for each strip.

These and other aspects of the present invention, therefore, provide an indication of a fault to a user in the event of a strip slackening, breaking, tearing, stretching or failing.

Other aspects and features of the present invention are contained in the appended claims.

These and other preferred aspects and features of the present invention will now be described purely by way of example with reference to the accompanying drawings.

DETAILED DESCRIPTION OF THE DRAWINGS

Figure 48:
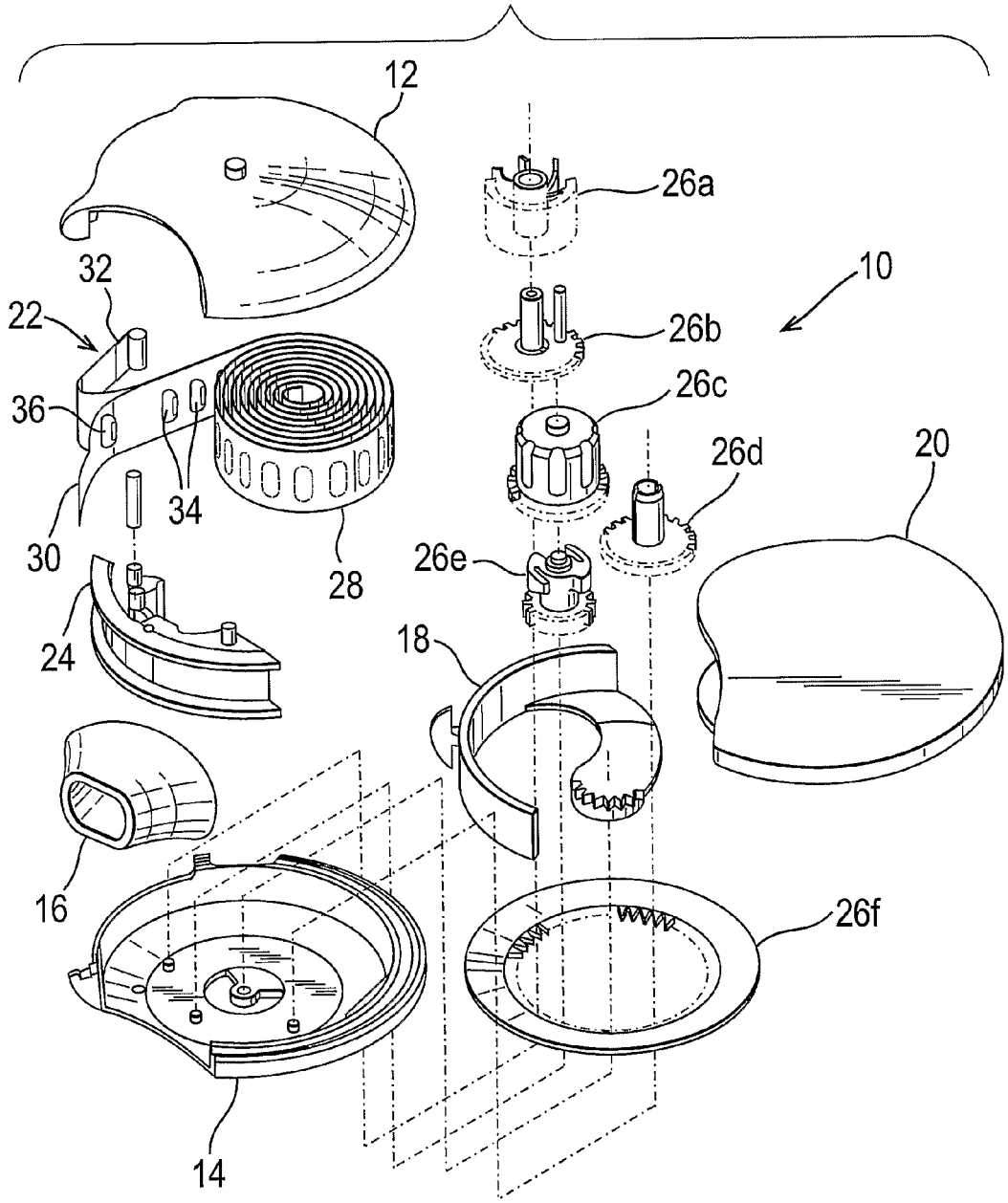
FIG. 48 is an exploded view of a prior art inhaler of a type suitable for adaptation to include a fault indicator of the present invention.

Referring first to FIG. 48, a prior art inhaler is shown. The inhaler (10) comprises two halves of a clam shell case (12,14) and a mouthpiece (16), a trigger (18), a rotatable cover (20), a strip (22), a strip guide (24) and gears, cogs or pulleys (26a,26b,26c,26d,26e,26f) of a strip advancement mechanism. The manner in which these components interact is explained in detail in U.S. Pat. No. 5,590,645. Accordingly, a detailed discussion of the strip advancement mechanism is not required. However, since a similar mechanism can be used in the present invention, it should be noted that the inhaler comprises a coiled source spool (28) from which the strip can be unwound for feeding around a path through the inhaler (10). Further, the strip (22) comprises a base sheet (30) and a foil cover sheet (32), as used in e.g. ADVAIR® DISKUS®. In the base sheet there are a plurality of blisters (34), each containing a premetered dose of medicament (not shown). By peeling away the cover sheet (32) from the base sheet (30), the medicament in the blisters can be released, one blister, and therefore one dose, at a time.

After peeling and release of the medicament, the base sheet (30) becomes coiled onto one of the lead pulleys (26d) and the cover sheet (32) becomes coiled onto the other of the lead pulleys (26a). The base sheet (30), however, prior to being coiled onto its lead pulley (26d), passes by the mouthpiece (16) for inhalation of the medicament contained in the most recently opened blister (36).

The present invention seeks to improve upon this prior art design by providing a fault indicator for the inhaler so that in the unlikely event of a breakage of the strip (22), or a component sheet (30,32) thereof, occurring, the user will know not to continue to use the inhaler (10) irrespective of whether the breakage results in the strip, or the component thereof, jamming the device. This is useful since the jamming of the device by the strip, or the component thereof, may not always occur.

Figure 1:
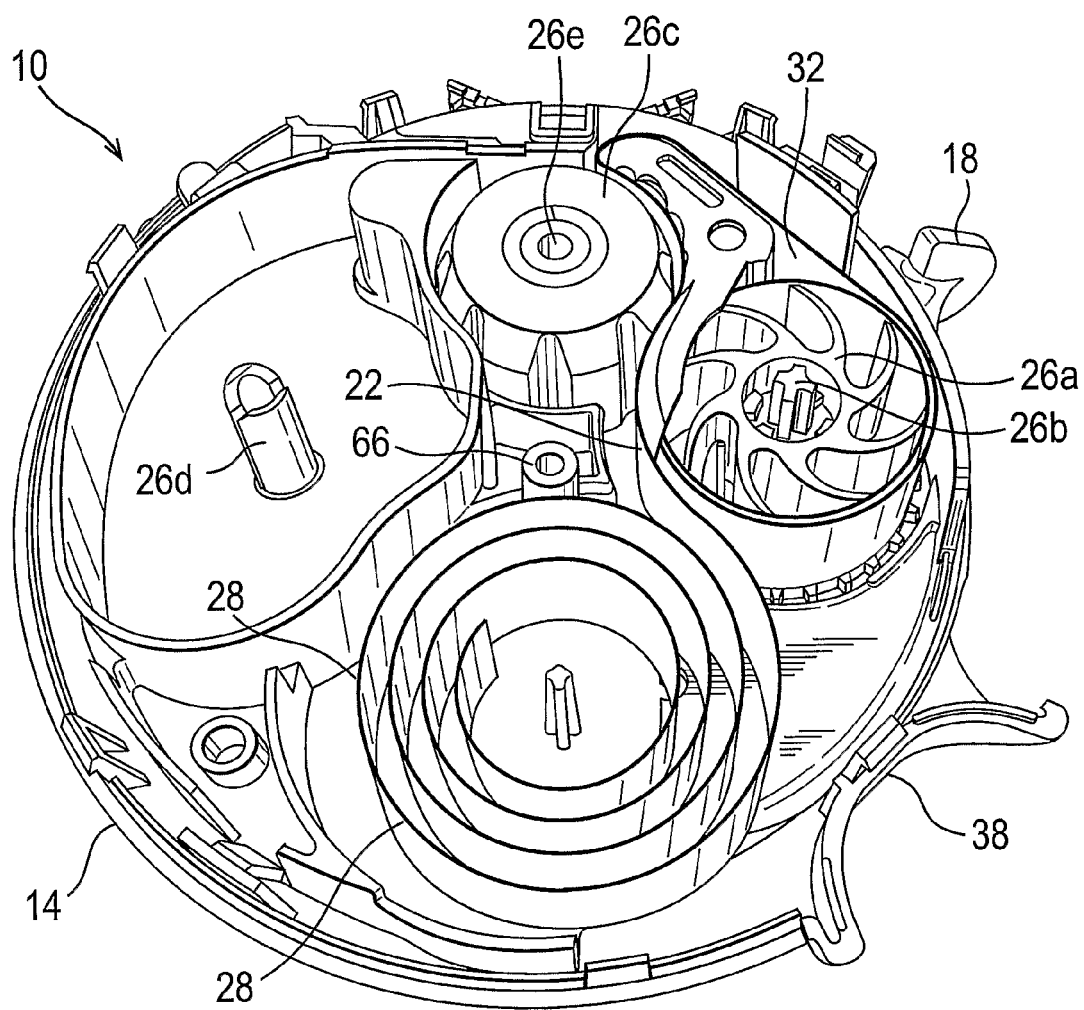
FIG. 1 shows the inside of a device in accordance with the present invention in a default state.

Referring now to FIG. 1, a preferred arrangement for the internal workings of a device of the present invention is shown. This device comprises a strip advancement mechanism that operates in a substantially similar manner to that shown in FIG. 48. It is not essential for the locations of the pulleys, however, to correspond exactly to that previously known. However, the positions of the various components, as illustrated, do generally correspond. Therefore, like elements have been provided with like reference signs.

Figure 2:
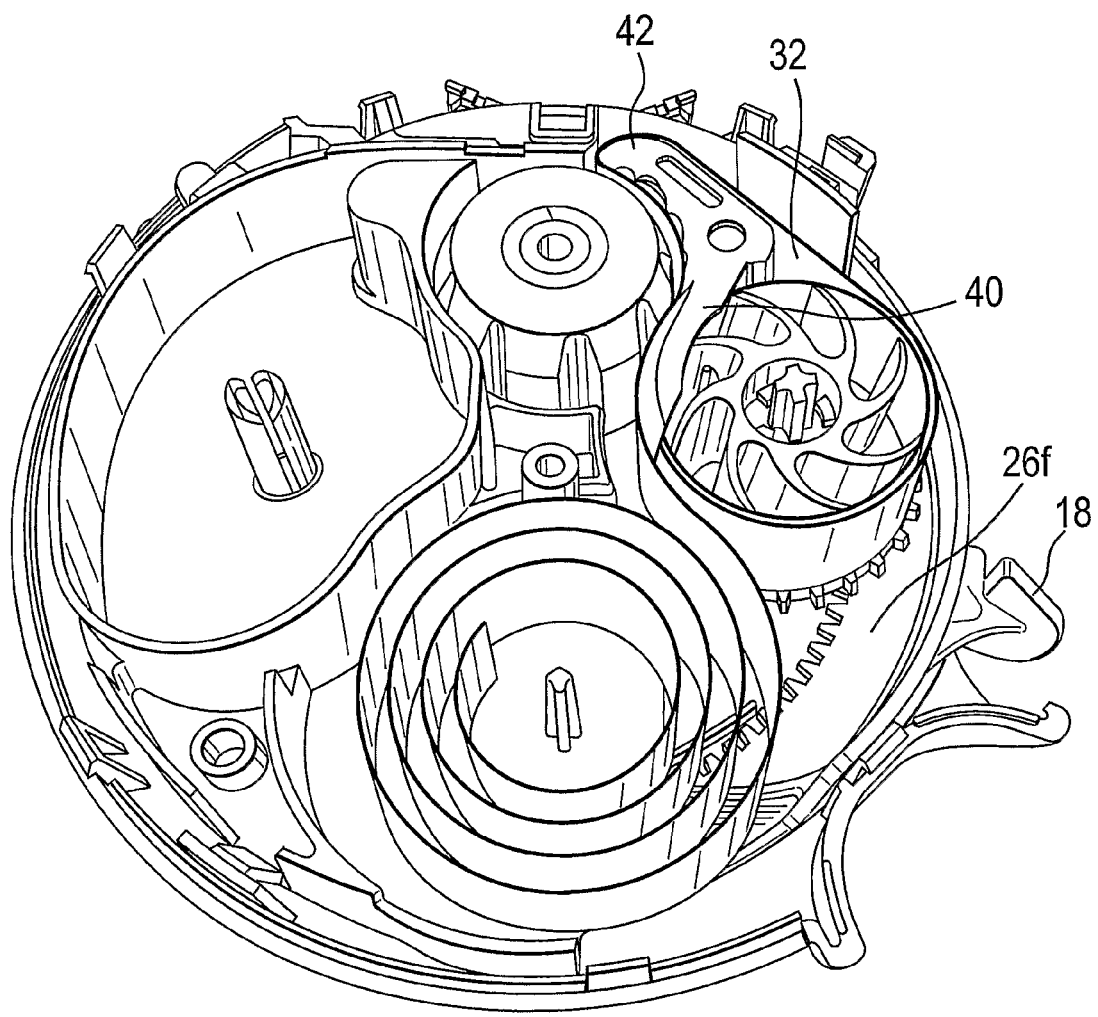
FIG. 2 shows the device of FIG. 1 in a trigger advanced state.

The device comprises a bottom half (14) of a clam-shell case, a trigger (18), and gears, cogs or pulleys (26a,26b,26c, 26d,26e,26f). The top half of the clam-shell case is not shown for clarity. Referring to FIG. 2, a planetary gear (26f) connecting various gears to each other can also bee seen. The planetary gear (26f) corresponds with the planetary gear (26f) shown in FIG. 48.

Advancing or triggering the trigger (18) (see FIG. 13) causes relative rotations of a guide pulley (26c) and the two lead spools (26a and 26d). They guide or pull the strip (22) through the device (10) along a predetermined path. At a predetermined point around the guide pulley (26c), the two layers of the strip are peeled apart. The cover sheet (32) then coils onto the first lead spool (26a) while the base sheet (not shown) coils onto the second lead spool (26d). Referring to FIG. 2, the peeling apart occurs at a nose portion or beak (42) of the device.

A finger grip (38) is provided on the case for assisting in the operation of the trigger (18).

Referring again to FIG. 2, the trigger (18) has now been rotated into its trigger advanced position (the representation, however, is only schematic so the Figure does not show any advancement of the source spool (28) or the strip).

The path of the cover sheet (32) of the strip (22) is clearly shown in FIGS. 1 and 2. The strip (22) feeds from the spool (28) along the path, which is defined by a manifold or base (40). This manifold or base (40) has guide surfaces for the strip (22) and the cover sheet (32). The guide surfaces include the side walls of the nose portion or beak (42). The beak (42), however, also defines the point at which the cover sheet (32) of the strip (22) is peeled away from the base sheet (not shown) of the strip (22). The beak (42) has a relatively sharp bend at this point (44), as more clearly shown in FIG. 3. This prevents too much of the cover sheet (32) from peeling off the base sheet (30) to ensure that just one blister is opened at a time. However, the point should be at least slightly rounded to prevent the cover sheet (32) from being cut.

Figure 3:
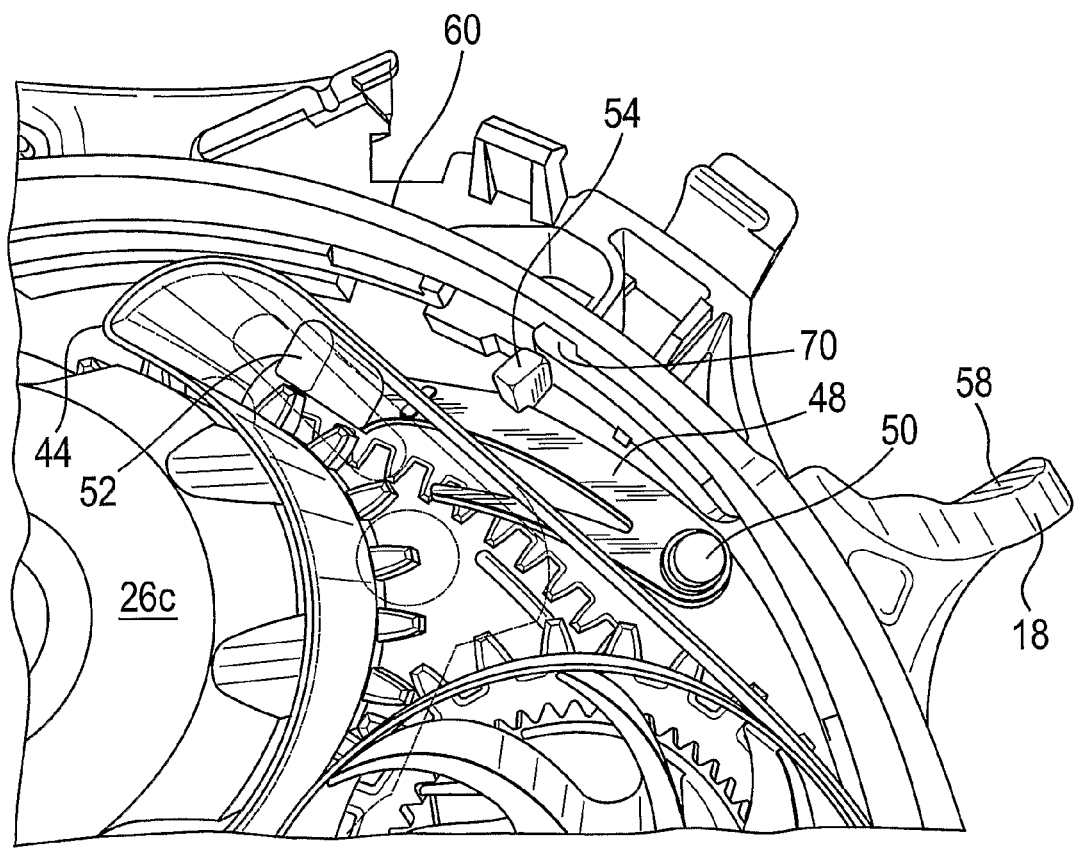
FIG. 3 shows a cut-away detail of FIG. 1, showing a first embodiment of fault indicator.
Figure 9:
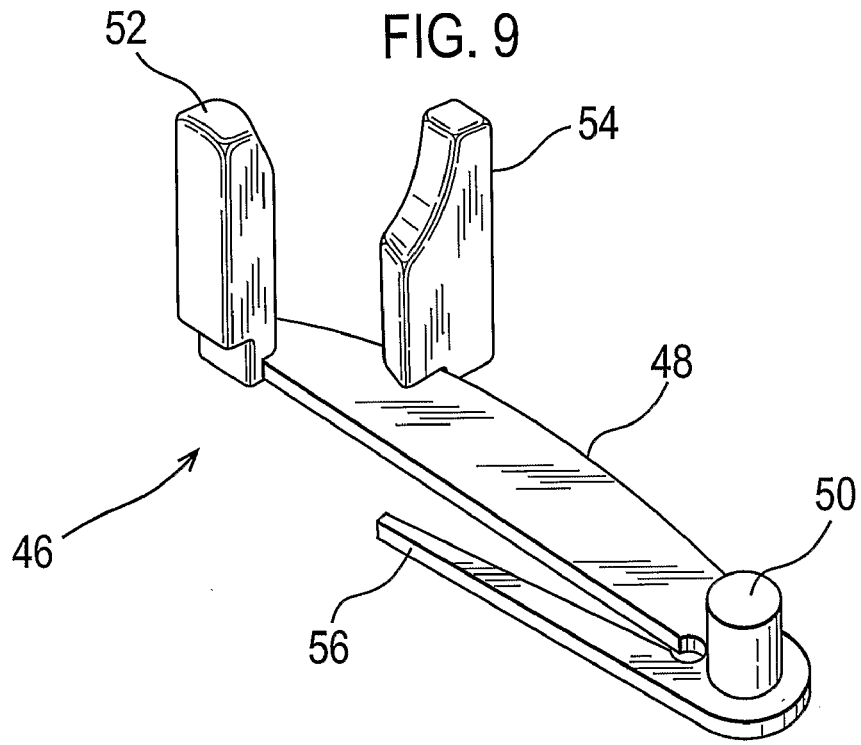
FIGS. 9 and 10 show a lever lock component of a fault indicator similar to that used in the embodiment of FIG. 3.
Figure 10:
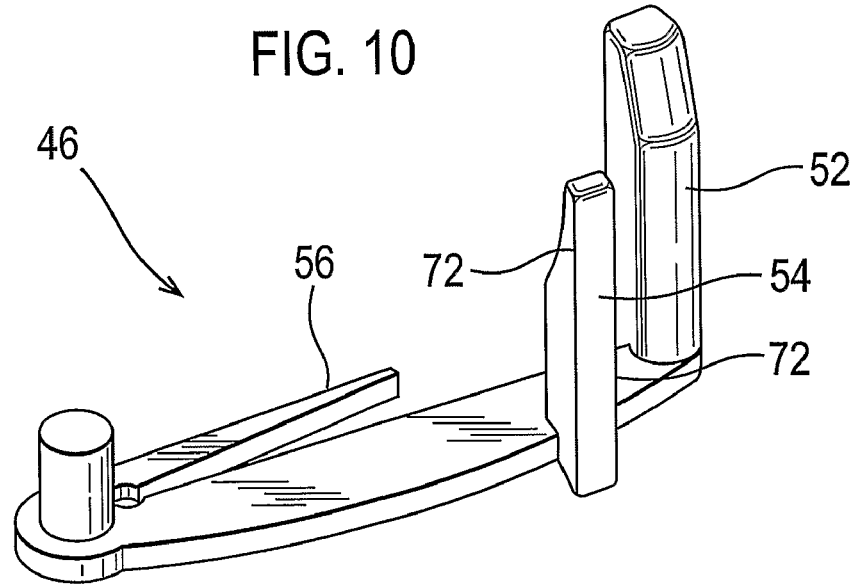
Figure 10A:
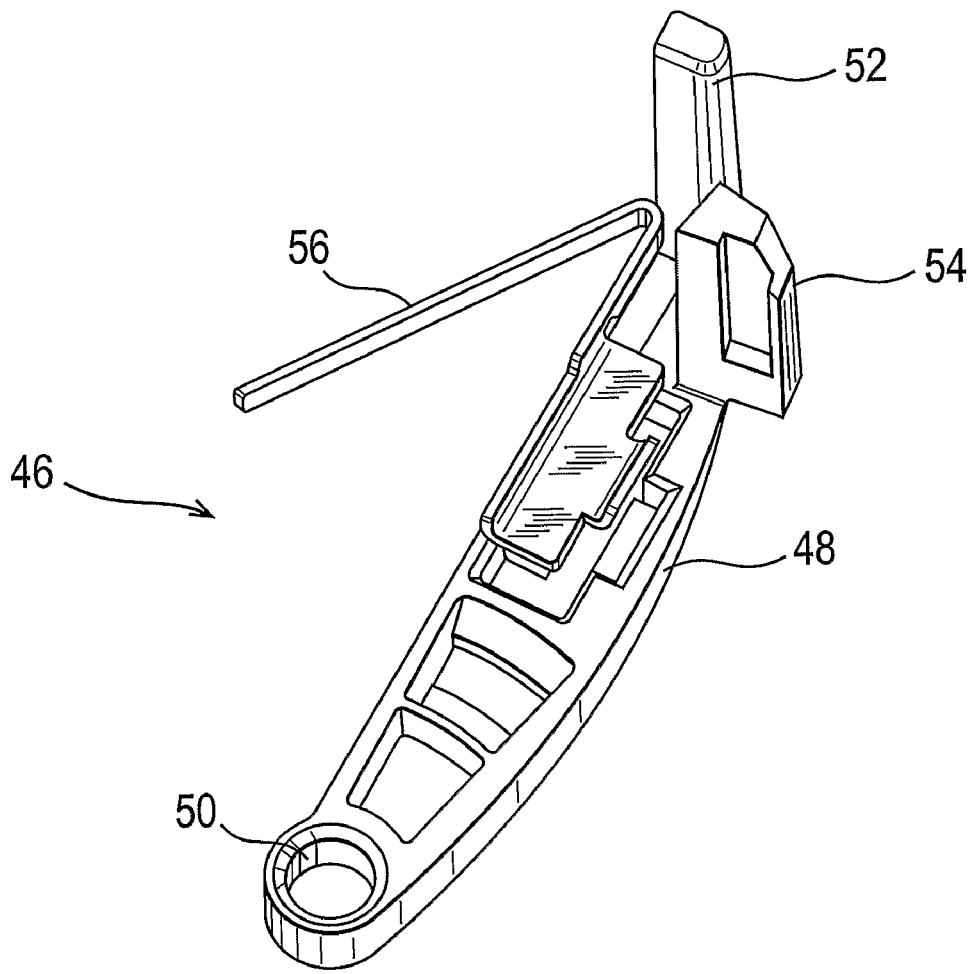
FIGS. 10A and 10B show an alternative lever lock component.
Figure 10B:
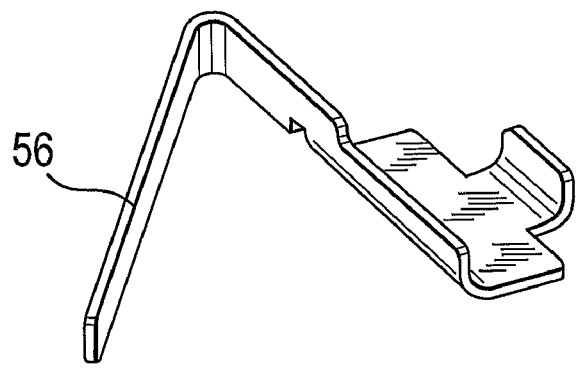
Figure 10C:
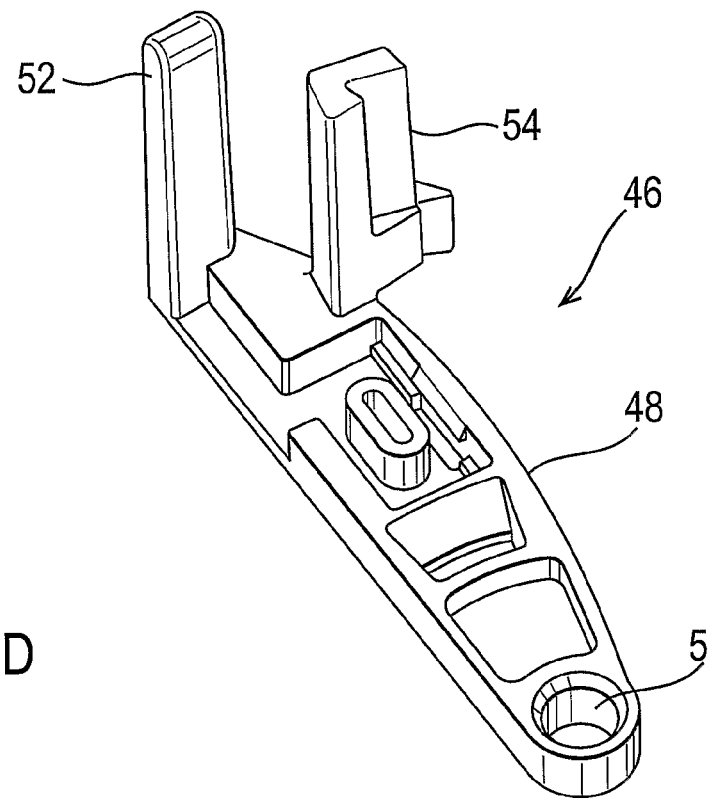
FIGS. 10C and 10D show a further alternative lever lock component.
Figure 10D:
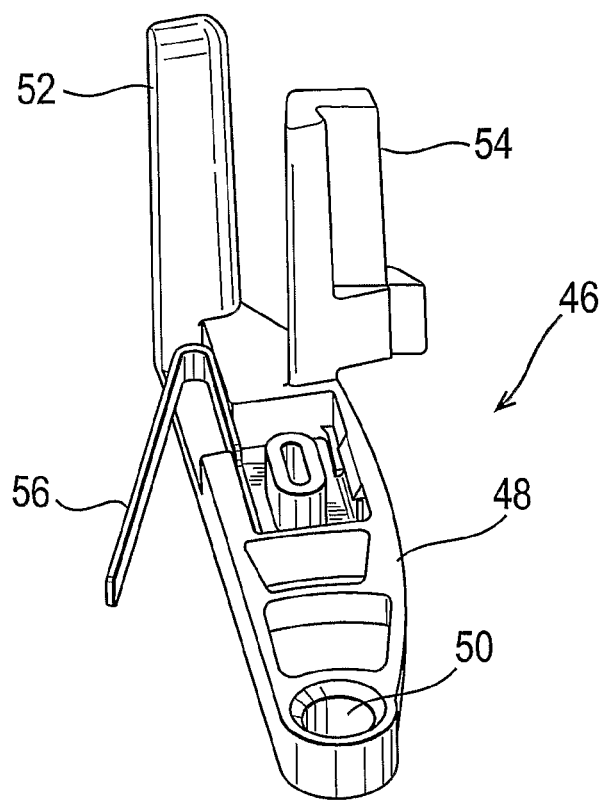

As also shown in FIG. 3, in which the manifold or base is illustrated as being transparent for showing the hidden components underneath it, a lever lock component (46) for a fault indicator of the present invention is provided. FIGS. 9 and 10 more clearly show this type of lever lock component (46).

The lever lock component (46) comprises a base (48) extending between a hub (50) and an element (52) for bearing against the strip (22), or the component (32) thereof. In use, the element (52) bears against the cover sheet (32). The element (52) therefore has a rounded bearing surface for bearing against the cover sheet (32) of the strip (22). By providing it with a rounded surface, it will not cause damage to the cover sheet (32) due to the bias of the element against the cover sheet (32). The cover sheet (32) is usually a foil cover sheet, thereby being prone to tearing if engaged by a sharp edge.

The hub (50) and the element (52) extend upwardly from the base (48) so that the base (48) will not interfere with the strip (22) or the component (32) thereof.

Extending both upwards and sideways from the base (48) there is also provided a blocking member (54). The blocking member (54) is spaced along the base (48) away from the hub (50) and close to the element (52).

The hub (50) forms a pivot axis for the element (52) and the blocking member (54). The hub (50), in use, will be located in a fixed aperture (106) (see FIG. 12) provided in the case or base of the device.

Figure 5:
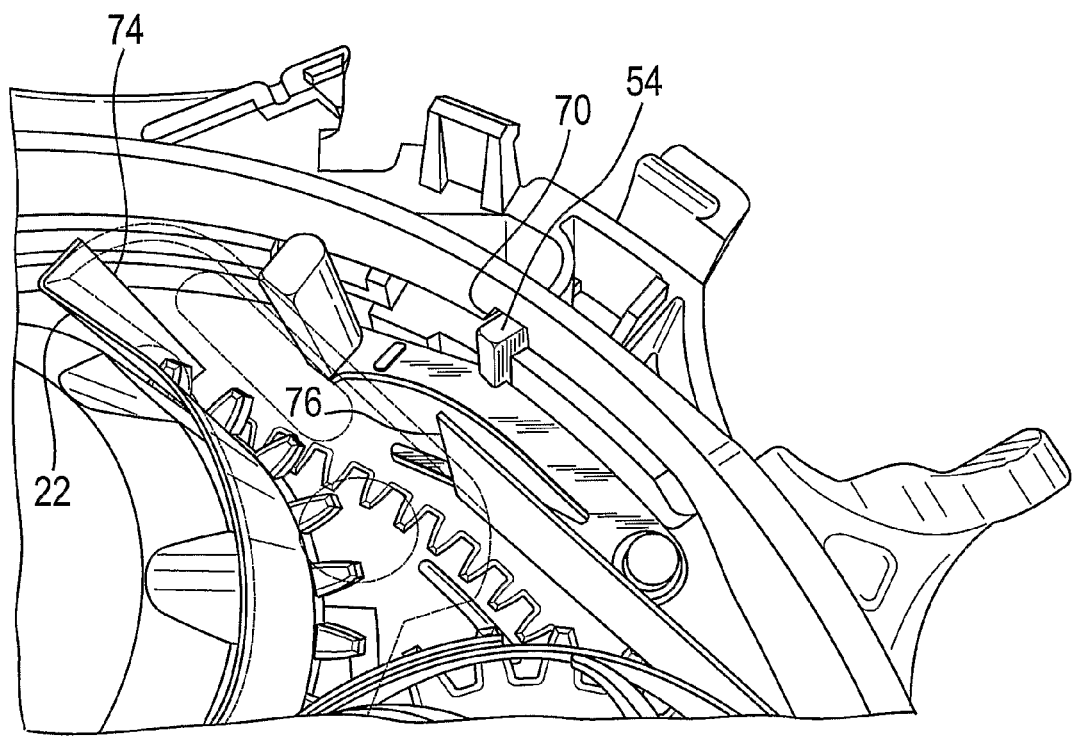
FIG. 5 shows the fault indicator in its fault indicating position and the trigger returned to its default state.

A resilient member or arm (56) is also integrally formed with the lever lock component (46). This arm (56) lies in the plane of the base (48). It is provided to provide the bias for the lever lock component (46) for moving it from the non-fault position, as shown in FIG. 3, to the fault indicating position, as shown in FIG. 5. The free end of the resilient arm (56) bears against a fixed fixture (not shown) in the device (10) to allow it to bias the lever lock component into its fault indicating position by rotating it about the axis of the hub (50).

Figure 13:
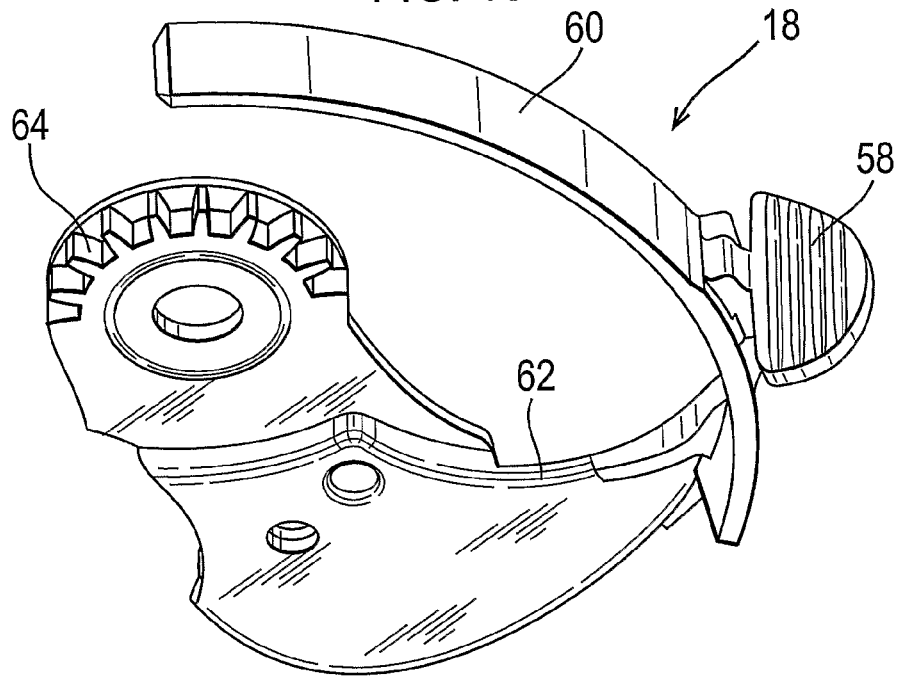
FIG. 13 shows a trigger for use with a device of the present invention for advancement of the strip advancement mechanism.

Referring now to FIG. 13, the trigger (18) comprises a finger pad (58) and a groove follower (60). The groove follower (60) defines an arc of a circle. From the inside face of the arc, an arm (62) extends to connect the groove follower (60) to a central gear drive member (64). The groove follower (60) and the central gear drive member (64) are concentrically arranged.

Figure 11:
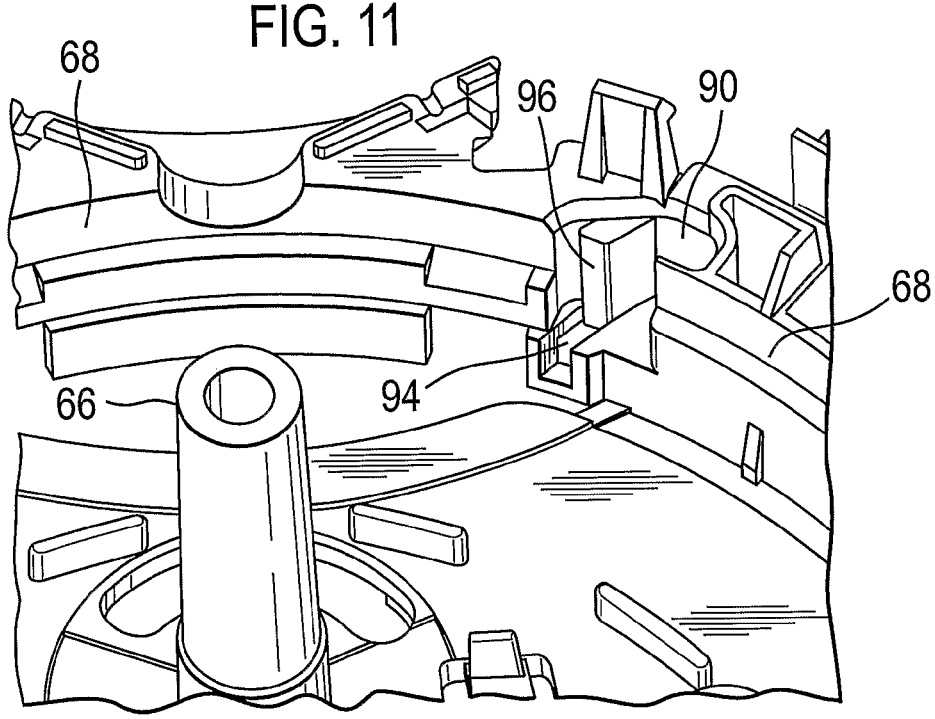
FIG. 11 shows details of a lower half of a case for a device, suitable for receiving the lever lock component of FIGS. 9 and 10.

The central gear drive member (64), in use, sits well down on a central hub (66) of the inhaler (10) (see FIG. 1, 2 or 11). The groove follower also sits in a groove (68) (see FIG. 4) provided around the perimeter of the base half (14) of the clam-shell case. Activation of the trigger causes the groove follower to slide in the groove (68) and the trigger (18) to rotate about the central hub (66) to provide a rotational motion for the gear drive member (64). The rotation of the gear drive member (64) interacts with the other components (e.g. gears) of the strip advancement mechanism, including the planetary gear (26f) and the lead spools (26a, 26d), to causes the strip (22) to advance.

For allowing the blocking of the strip advancement mechanism, the groove follower (60) comprises a recess or hole (70) in its inside surface. This recess (70) may be a through hole. Preferably, however, it is not, so as to limit dust ingress into the device.

The recess (70) is positioned in the groove follower (60) in such a position that when the trigger (18) is in its default position, as shown in FIG. 3, the recess aligns with the blocking member (54). This is so that upon rotation of the lever lock component (46) about the hub (50), i.e. upon encountering a fault in the strip, the blocking member (54) will move into engagement with the recess (70) as the trigger's recess comes into registration with the blocking member (54). This will then cause a blocking, or lock-out, function for the trigger (18) to prevent further activation of the trigger (18).

Referring now to FIG. 10, the blocking member (54) has sharp edges (72). Similarly, the recess (70) has sharp edges (not shown). The interaction between the recess and the blocking member, therefore, is positive and secure. This provides a secure blocking of the trigger (18).

Although the recess (70) is shown to be in registration with the blocking member (54) when the trigger is in its default state, it would be possible to put the recess elsewhere along the groove follower. For example, it could be positioned such that it would be in registration when the trigger (18) is at a trigger advanced position. However, placing the recess in registration with the blocking member (54) when the trigger (18) is in its default position reduces the opportunity for a user to bypass the blocking feature accidentally, for example by just partially actuating the trigger (18).

Preferably the trigger is biased back to its default position, for example, by a tension spring (not shown), so that it would return to that default position whenever the device or inhaler is not in use.

Figure 4:
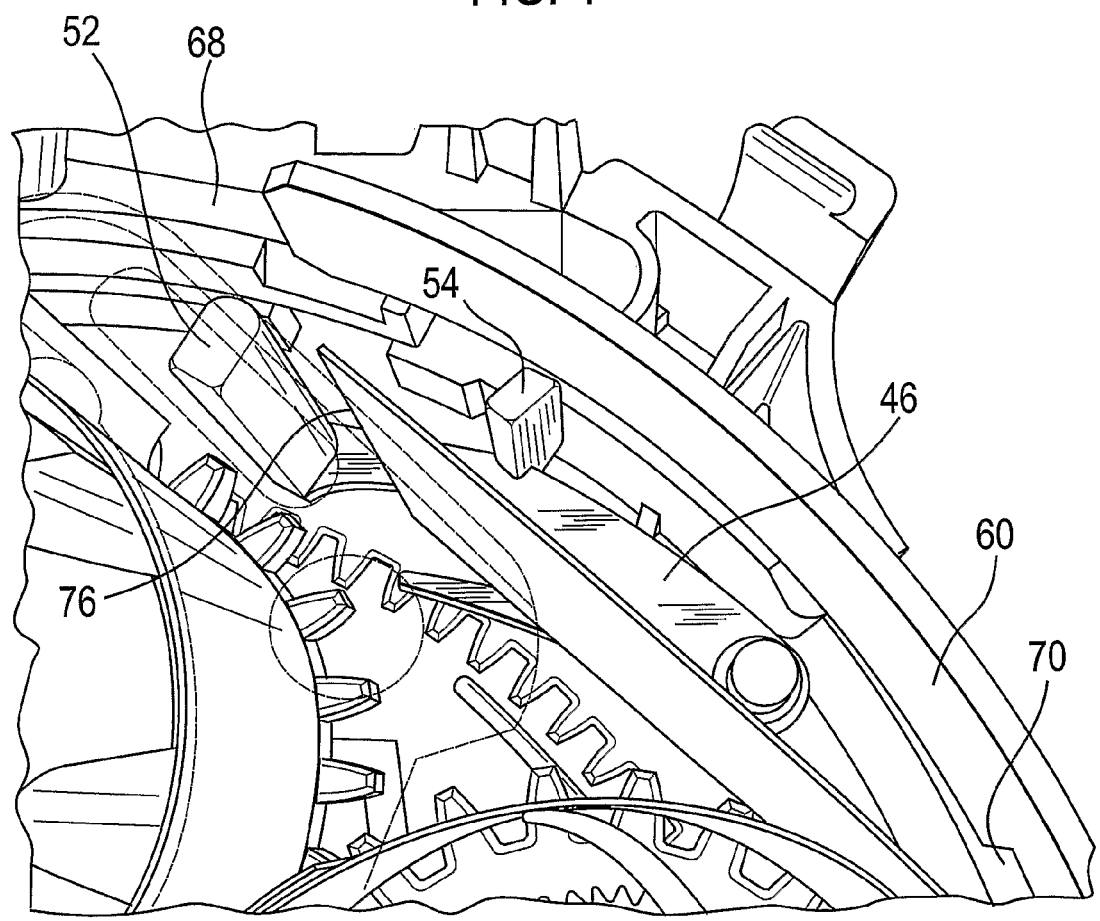
FIG. 4 shows a cut-away detail, similar to FIG. 3, but in a trigger advanced state, and in which a fault has developed in the strip, the fault indicator being about to move towards a fault indicating position.

FIG. 5 shows the blocking member (54) in engagement with the recess (70) in the groove follower (60). This fault indicating position (the fault being indicated by the inability of the trigger (18) to be actuated) for the lever lock component has been reached since the strip (22) has developed a fault and is no longer continuous—see the two open ends (74,76) of the cover sheet (32). Referring to FIG. 4, however, the lever lock component (46) has not yet rotated into its fault indicating position. This is because the blocking member (54) is not in registration with the recess (70) in the groove follower (60) while the trigger (18) is in its trigger advanced position. Upon returning then trigger (18) to its default position, however, as shown in FIGS. 1, 3 and 5, the recess (70) would be moved back into registration with the blocking member (54). The lever lock component (46) would then rotate to its blocking position, i.e. the fault indicating position of FIG. 5.

Referring now to FIG. 11, a detailed view of part of a lower case for an inhaler comprising the lever lock component of FIGS. 9 and 10 is shown. The lower case comprises a groove (68) for the groove follower (60). The groove (68) is open on one side—i.e. a rebate or square V groove. A manifold guide slot (90) is also provided, spaced radially outward from the groove (68), for receiving a manifold guide or key (92) that is provided in the manifold or base—see FIG. 12. The registration of these two "key" components during assembly ensures that the manifold is positioned correctly within the lower case.

Adjacent to the manifold guide slot (90) is a slot (94) for receiving and guiding the blocking member (54) of the lever lock component (46). The slot (94) extends radially to a stop (96). Either the back of the groove follower (60), or, if the groove follower has a through hole recess, the flat end of the blocking member (54), will usually bear against this stop (96) when the lever lock component (46) has been biased into its fault indicating position.

Figure 12:
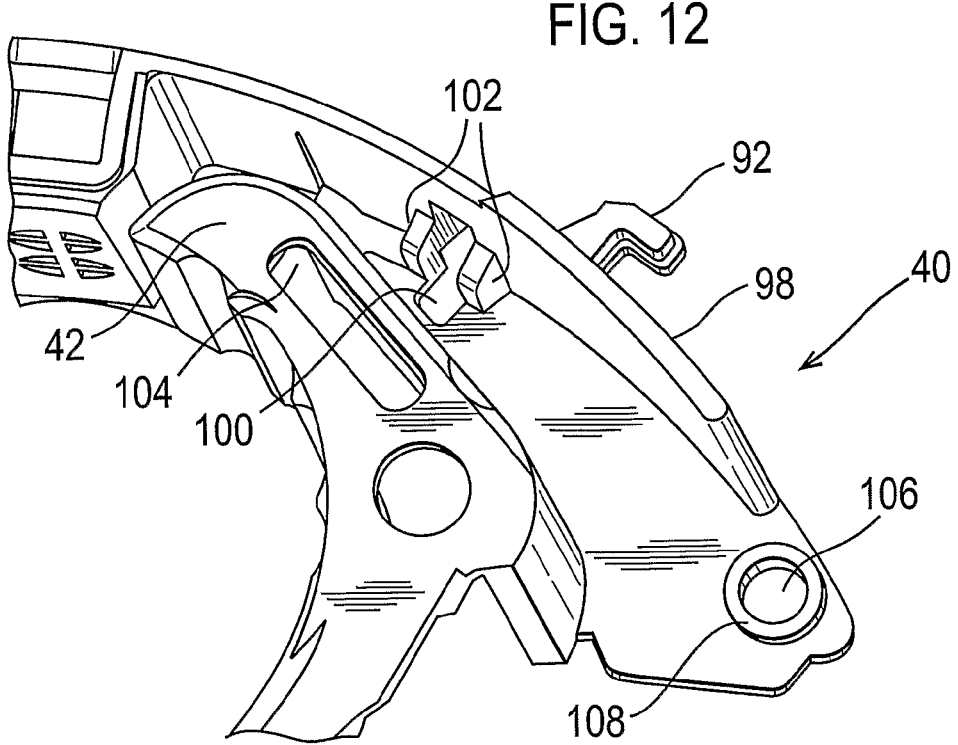
FIG. 12 shows a manifold, or base, for fitting into the lower half of the case of FIG. 11.

Referring now to FIG. 12, the manifold guide or key (92) extends radially away from an outer wall (98) of the manifold or base (40). A slot (100) is provided in the manifold or base (40) for receiving and guiding the blocking member (54) of the lever lock component (46). It will also be in registration with the slot (90) in the lower case. Reinforcement blocks (102) are located either side of the slot (100) in the manifold for guiding the blocking member (54) and for providing reinforcement for the blocking of the trigger upon movement of the lever lock component (46) into its fault indicating position. The blocks (102) also help to ensure that the blocking member will not be bent if firm attempts to actuate the trigger (18) are made.

The manifold or base (40) shown in FIG. 12 comprises the nose portion, or beak (42). The nose portion has side walls that define the path for the strip (22), or the component (32) thereof. In one side wall, after the tip of the nose portion, an aperture or cut out is provided. The element (52) of the lever lock component (46) extends through this aperture so as to be able to engage or bear against the cover sheet (32) as it passes along the path. The length of the path extending over the aperture is the fault sensing portion of the path.

The base (48) of the lever lock component (46), during assembly, is sandwiched between the lower case of FIG. 11 and the manifold (40) of FIG. 12. The element (52) extends into the aperture or cut out (104) in the manifold. The hub (50) extends through a hole (106) in the manifold for rotation relative to the manifold. The hole (106) is reinforced by a flange (108), which is moulded in the manifold (40). The blocking member (54) extends through the slot (100) provided in the manifold or base (40). A flange (not shown) can also be provided, preferably depending from the base of the manifold (40), for the resilient arm (56) of the lever lock component (46) to bear against in order to bias the lever lock component (46) from its non-fault position to its fault indicating position. The flange, however, might instead extend upward from the lower case.

In FIGS. 10A and 10B and FIGS. 10C and 10D there are two alternative lever lock components (46) having like features to the lever lock component (46) of FIGS. 9 and 10, which like features are given like reference numerals. The alternative lever lock components (46) are to perform the same function as the lever lock component (46) of FIGS. 9 and 10, the principal differences embodied in the alternative lever lock components (46) being as follows:— i) The alternative lever lock components (46) are formed from two separate parts, a spring part comprising the resilient member (56) and a body part comprising the base (48), the hub (50), the strip bearing element (52) and the blocking member (54). The spring and body parts are able to be fixed together to form the lever lock component (46), e.g. through a snap fit, an interference fit or some other interconnection. In this instance, the spring part is made from any suitable metal, for instance spring steel, and the body part is formed from a plastics material, e.g. by moulding. Having a separate spring part enables the resilient member (56) to be formed more strongly than may otherwise be possible if the lever lock component is made (e.g. moulded) as a one-piece component made from a plastics material. In particular, this avoids any potential problem with creep in a one-piece plastic component for this application.

ii) The resilient member (56) is disposed at the opposite end from the hub (50).

iii) The hub (50) is a female feature locatable in a male feature (not shown) provided in the case or base of the device.

In the afore-described fault indicator embodiments utilising a lever lock component (46), instead of the blocking member (54) locking the trigger (18) by insertion into the recess (70) in the groove follower (60) of the trigger (18), the blocking member (54) may simply move in front of the free end of the groove follower (60). In this case, the recess (70) would be dispensed with and, after the trigger (18) is moved further clockwise as viewed in FIG. 4, the free end of the groove follower (60) would pass the blocking member (54) so that, in the event of a strip failure, the blocking member (54) would be biased into the groove (68) so as to sit in front of the free end of the groove follower (60) preventing full return movement of the trigger (18) and hence any subsequent actuation of the device.

For the lever lock component embodiments, it may be useful to have a lighter grade of paper in the cover sheet (32) than currently used in ADVAIR® DISKUS®.

Figure 6:
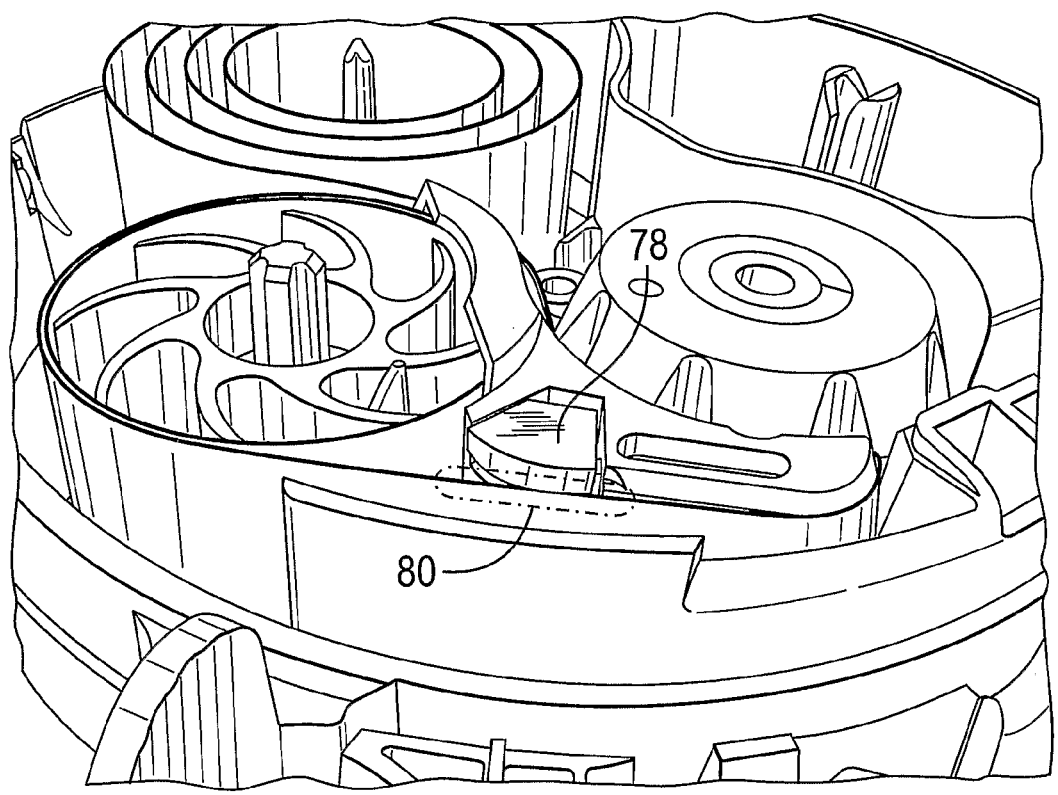
FIG. 6 shows an alternative embodiment of fault indicator in a device having a substantially similar strip advancement mechanism as that shown in FIG. 1, with no fault in the strip.
Figure 8:
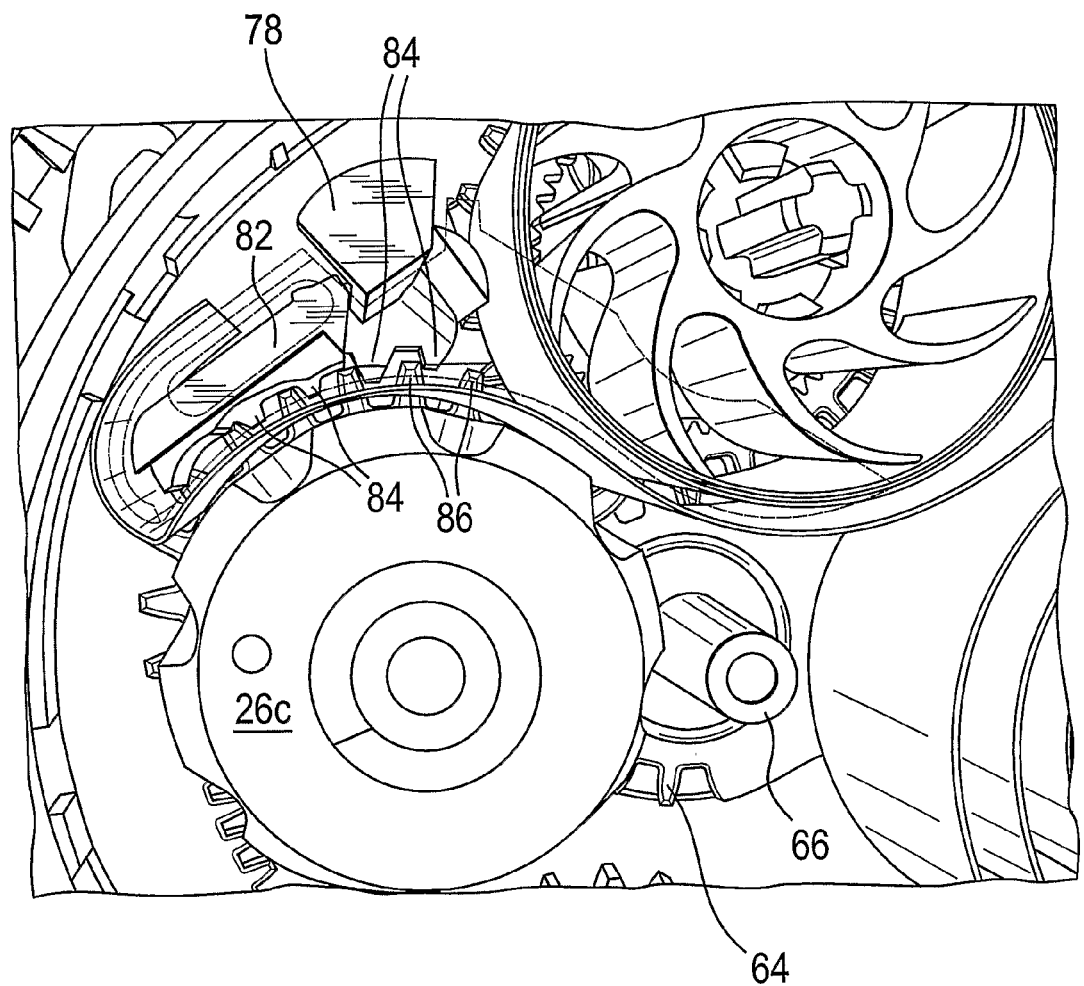
FIG. 8 is a cut-away view of the fault indicator of FIGS. 6 and 7 in the fault indicating position of FIG. 7, showing blocking elements engaging teeth of a gear of the strip advancement mechanism.

Referring now to FIG. 6, an alternative embodiment of fault indicator (82) is shown. The fault indicator (82) comprises a tab (78) at its top which in a non-fault position rests on the edge of the cover sheet (32) of the strip (22), as shown in FIG. 6. At the bottom of the fault indicator (82), a toothed strip advancement resisting means (84) is provided, as shown in FIG. 8 which is a cutaway view, from above, of the fault indicator (82) in its fault indicating position. In this embodiment, the toothed strip advancement resisting means (84) takes the form of a tooth profile, but other gear locking structures could be employed.

The fault indicator (82) is mounted within the nose portion (42) of the manifold or base (40). An aperture (88) is provided in the nose portion (42) for the tab (78) to pass through for engagement with the edge of the foil cover sheet (32). This aperture is provided in the top wall of the manifold (40) for the illustrated embodiment.

Figure 7:
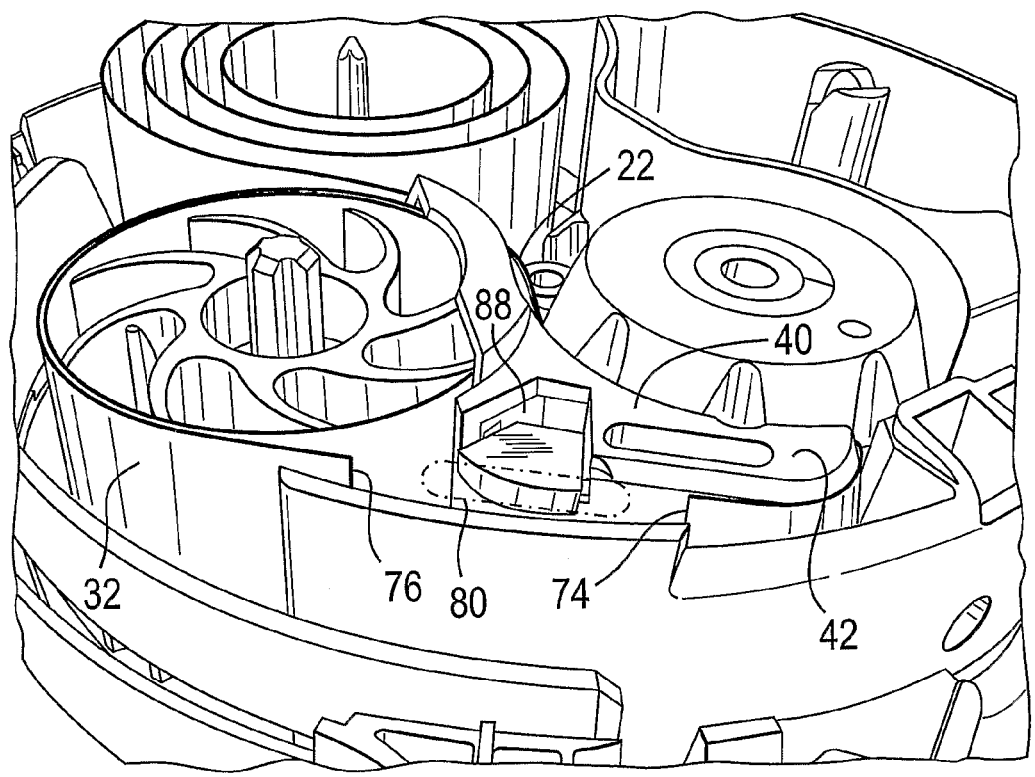
FIG. 7 shows the fault indicator of FIG. 6 in a fault indicating position.

In FIG. 7, when two open ends (74,76) are formed in the strip (22) to open up a gap therebetween (i.e. a fault condition), the tab (78) is free to move through the plane usually followed by the cover sheet (32) through the fault sensing portion (80) of the path. This results in movement of the fault indicator (82) to its fault indicating position. The travel of the fault indicator (82) may be one or two millimeters from its non-fault position.

In the non-fault position, the toothed strip advancement resisting means (84) is spaced away from, i.e. out of engagement with, teeth (86) of a gear at the base of the guide pulley (26c). However, upon movement of the fault indicator (82) to its fault indicating position, as shown in FIGS. 7 and 8, the toothed strip advancement resisting means (84) moves or drops into meshing engagement with the teeth (86) of the guide pulley (76c) to block further movement thereof. The guide pulley (76c) forms part of the strip advancement mechanism of the device (inhaler), whereby this blocking action by the strip advancement resisting means (84) prevents further advancement of the strip, thus indicating to the user that a strip failure has occurred.

If desired, the tab (78) can also function as a visual fault indicator by providing in the top half of the clam-shell case (not shown) a window (80) which is positioned to be in registration with the tab (78) when the tab (78) has moved into its fault indicating position, as shown in FIG. 7.

Instead of blocking movement of the teeth (86) of the guide pulley (26c), the depth of the meshing of the toothed strip advancement resisting means (84) can be adapted to allow further attempts to advance the strip advancement mechanism to ratchet the teeth (86) past the toothed strip advancement resisting means (84). This ratcheting provides an audible sound for alerting the user to the fault, thereby also providing a tactile and audible indicator to the user. In this regard, the teeth may mesh with the toothed strip advancement resisting means by about 1mm, or more preferably by up to about half the depth of the teeth.

Figure 14:
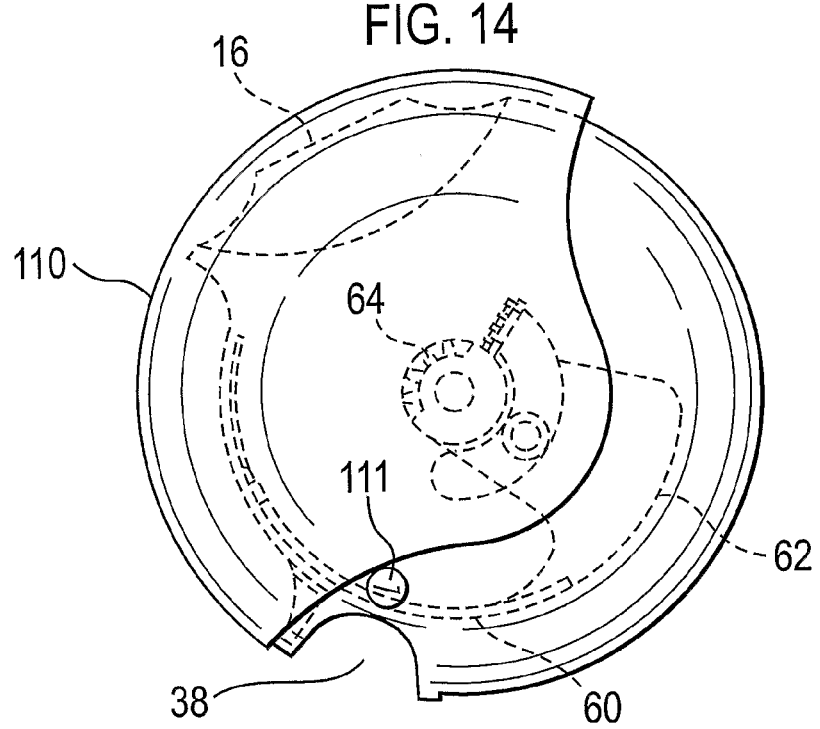
FIG. 14 schematically shows an inhaler device similar to that of FIG. 1, in the default state, which is suitable for fitting with a fault indicator in accordance with the present invention.
Figure 15:
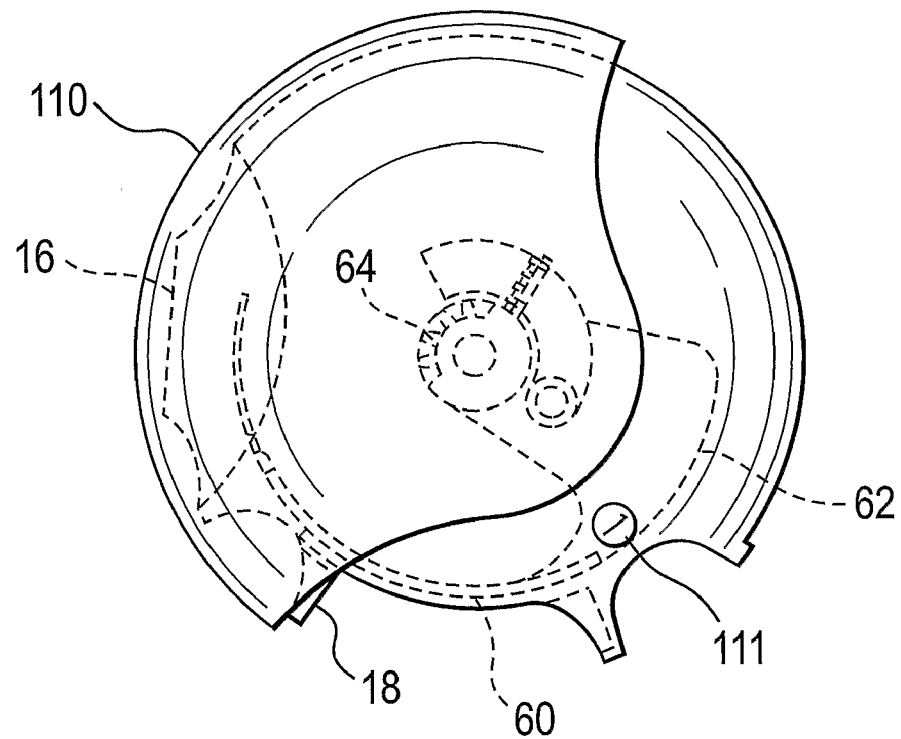
FIG. 15 shows the device of FIG. 14 in a trigger advanced state.

An assembled device or inhaler of the present invention can have the appearance as generally shown in FIGS. 14 and 15. The device comprises a rotatable cover (110), as shown in more detail in FIG. 16. It also includes a dosing counter (111), as known in the art. As shown, the trigger (18) has an alternative arrangement to that of FIG. 13—the arm (62) extends from a different part of the groove follower (60). However, the gear member (64) still functions in the same way as previously described for driving the strip advancement mechanism.

In FIG. 14, the trigger is in its default state.

Figure 16:
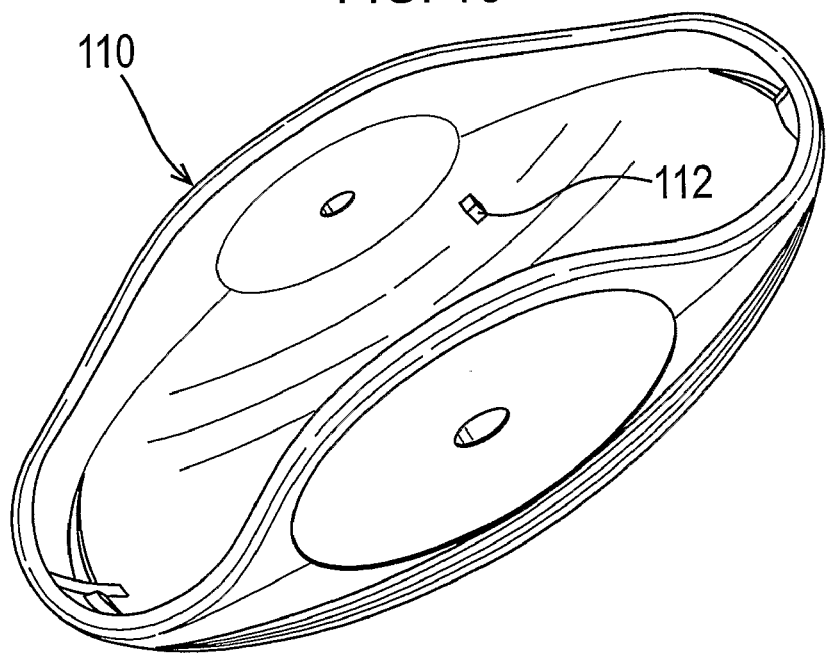
FIG. 16 shows a detail on the inside of a rotatable cover of the device of FIGS. 14 and 15.

The trigger is engaged by a notch (112) of the rotatable cover (110) (see FIG. 16). The notch (112) is provided in an inside wall of the rotatable cover (110). Because of the notch, the trigger can be advanced to its trigger advanced position, as shown in FIG. 15, simply by rotating the rotatable cover. This eases the operation of the device. However, the finger pad (58) provided for the trigger (18) can still be used if preferred. However, in the arrangement shown in FIGS. 14 and 15, the trigger's finger pad (58), when the trigger (18) is in its default position, as shown in FIG. 14, is recessed into a side wall of a finger grip (38) for the case. In this position, the finger pad (58) of the trigger (18) cannot easily be accessed for trigger activation, other than by rotation of the rotatable cover (110) first.

The use of this notch (112) is an additional safety device—if the blocking member (54) is in engagement with the recess (70) in the groove follower (60) of the trigger (18), any attempt to rotate the rotatable cover (110) will be opposed due to the trigger being blocked. However, if the attempt is firm enough, the notch (112) will fail or snap off, thereby being removed from its engagement with the trigger (18). Then, further actuation of the trigger (18), whose finger pad (58) is in the recess of the finger grip (38), will be made more difficult.

Figure 17:
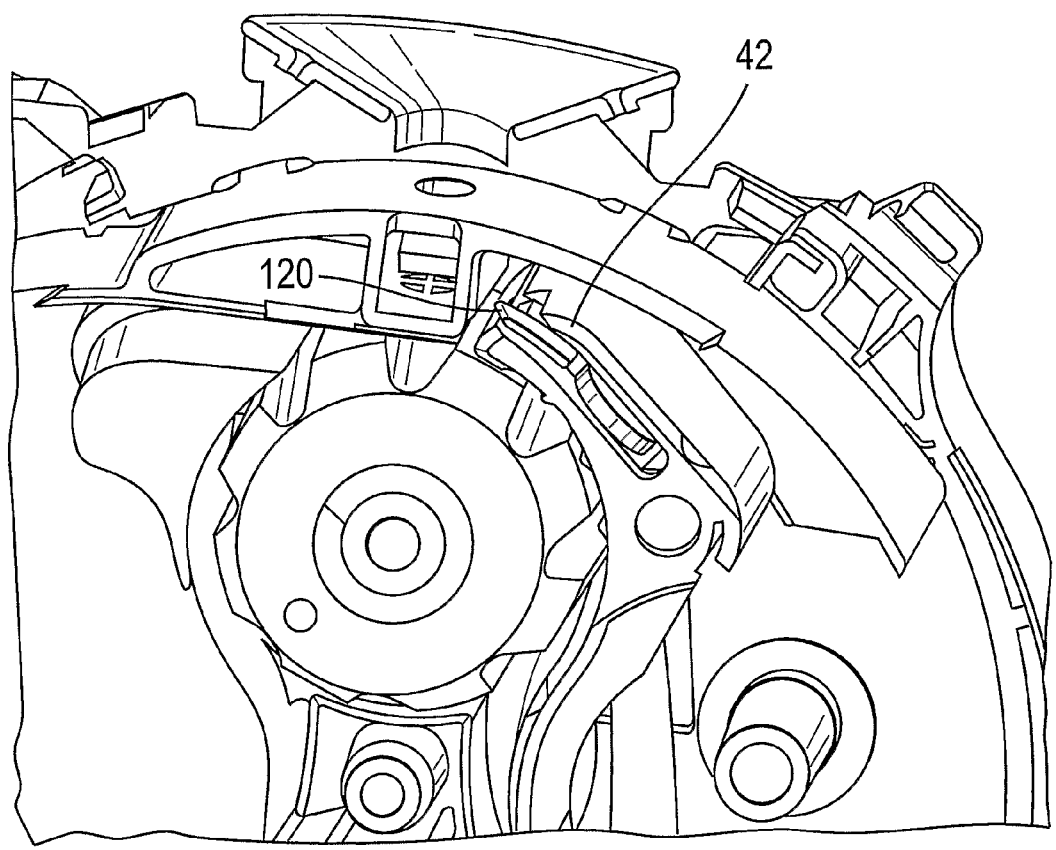
FIG. 17 shows a further embodiment of fault indicator in accordance with the present invention, having a dropping piston design.
Figure 18:
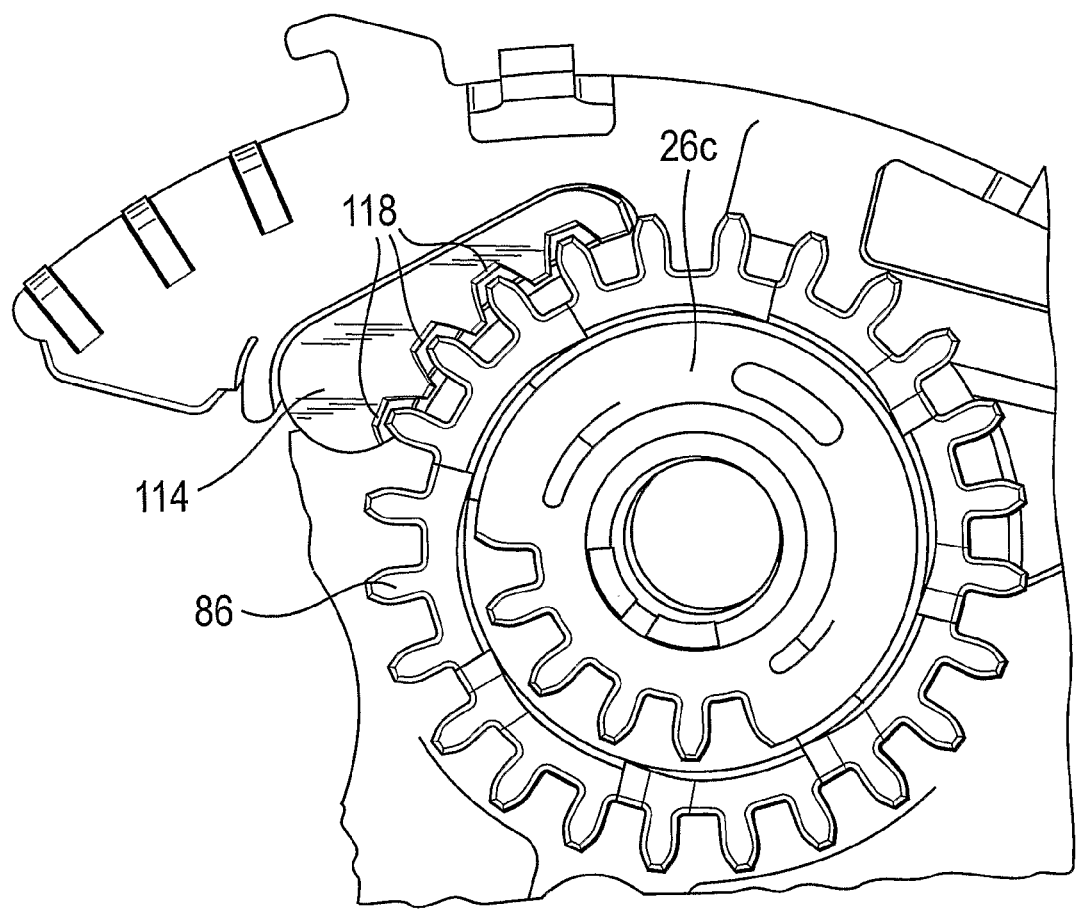
FIG. 18 is an underneath, cut-away, plan view of the embodiment of FIG. 17 showing the engagement of the bottom of the piston with teeth of a guide pulley of the strip advancement mechanism.
Figure 19:
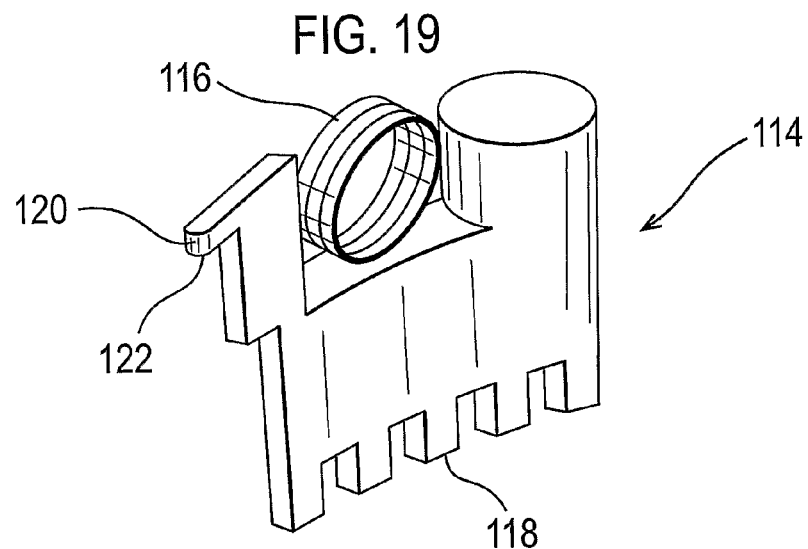
FIG. 19 is a perspective view of a dropping piston for the embodiment of FIG. 17.

Referring now to FIGS. 17, 18 and 19, a third type of fault indicator is disclosed. This fault indicator comprises a dropping piston arrangement. The piston (114) is shown in FIG. 19, although other arrangements for the piston are possible.

The piston (114) comprises a resilient member (116), in the form of a resilient hoop, provided at the top of the piston (114). This hoop is integrally formed with the piston (114). The bottom of the piston comprises a toothed arrangement, as shown in plan, from below, in FIG. 18. This toothed arrangement (118) is adapted to fit over and mesh with teeth (86) of the guide pulley (26c), similar to that previously described in relation to the embodiment of FIG. 8. The mesh depth is preferably 1 mm.

The piston (114) is adapted to actuate by movement linearly downward, from the position shown in FIG. 17, i.e. the non-fault position, into a position that is in engagement with the teeth (86) of the guide pulley (26c), i.e. the fault indicating position. As before, the resilience of the resilient member (116) defines the force with which the toothed arrangement (118) can resist or block further motion of the guide pulley (26c). However, the resilient member should not impose a large level of bias, as: explained below, so the toothed arrangement preferably will more positively, or more deeply, mesh with the teeth (86) of the guide pulley (26c).

Preferably the downward motion involves a 1.5 mm travel.

The hoop (116) may be replaced by any other appropriate resilient member.

Referring again to FIG. 19, the piston (114) comprises an element (120) for bearing against a side of the cover sheet (32) as the sheet (32) passes around the nose portion (42). The cover sheet (32) is not shown in FIG. 17. Nevertheless, the non-fault position of the element (120) is shown in that figure.

The underside (122) of the element (120) bears against the side or edge of the cover sheet (32). The element (120) is biased downwards by the resilient member. Therefore, upon a fault in the cover sheet passing through the fault sensing portion of the path, the piston (114) will cease to have a cover sheet to bear against and it will drop into its fault indicating position. The toothed arrangement (118) at the bottom of the piston will therefore be moved into engagement with the teeth (86) of the guide pulley (26c) for causing a blocking or ratcheting effect upon further activation of the device.

The spring bias offered by the resilient member should be sufficient to cause the drop, but insufficient to significantly crush the side of the cover sheet. It is for this reason that a weak spring force is desirable. A hoop spring, therefore, is particularly suited for this purpose.

Figure 20:
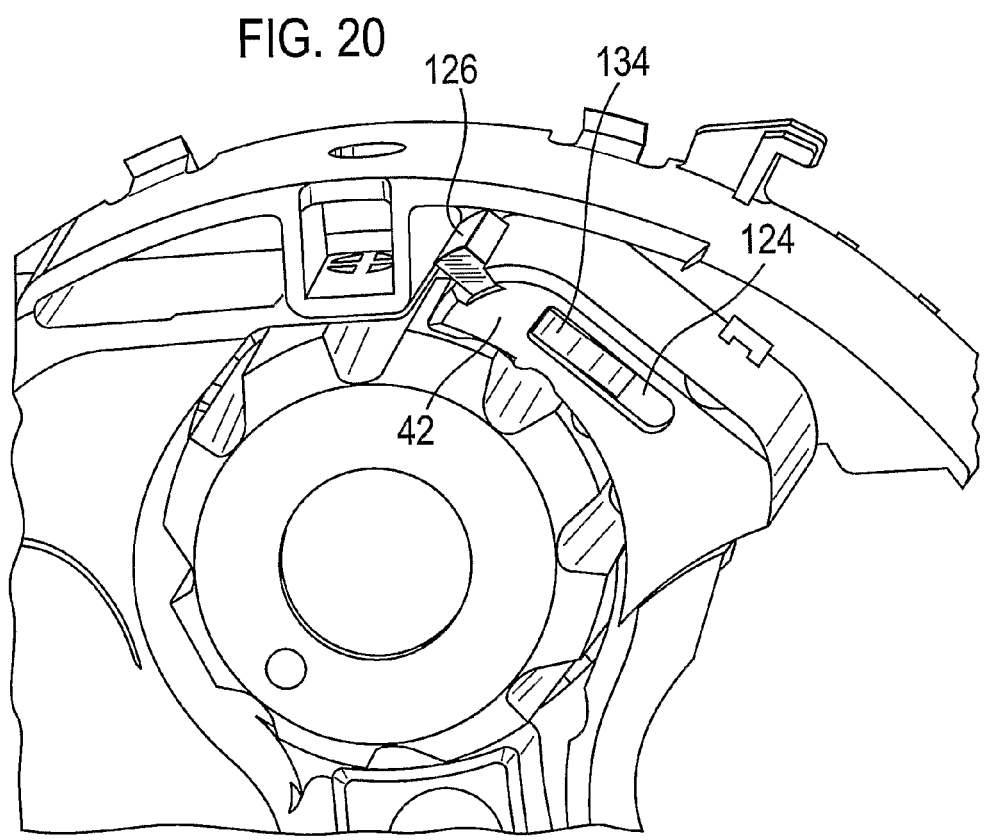
FIG. 20 shows a further embodiment of fault indicator in accordance with the present invention.
Figure 21:
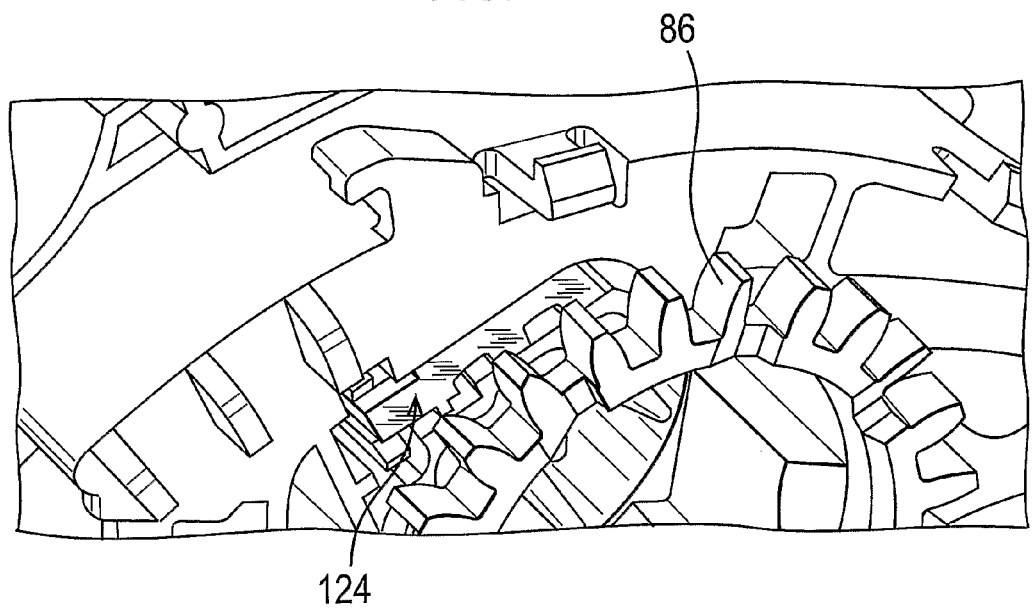
FIG. 21 shows an underneath, cut-away, perspective view of the fault indicator of FIG. 20 in a non-fault position.
Figure 22:
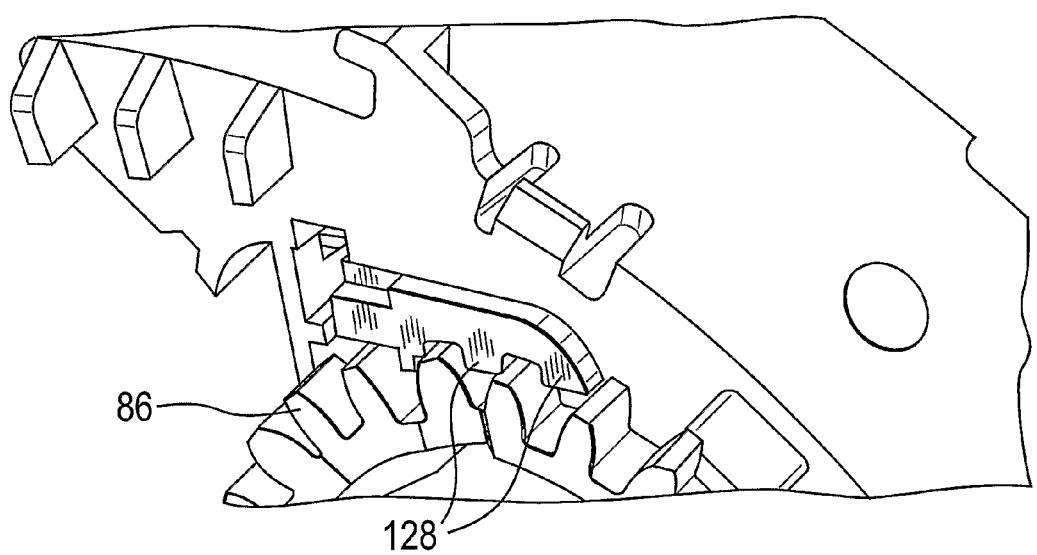
FIG. 22 shows an underneath, cut-away, perspective view of the fault indicator of FIG. 20 in a blocking, or strip advancement resisting, position.

Referring now to FIGS. 20, 21 and 22, a fourth type of fault indicator is shown. This fault indicator also involves a piston (124). The piston comprises an element (126) that extends through an aperture in the end of the nose portion or beak (42).

Figure 23:
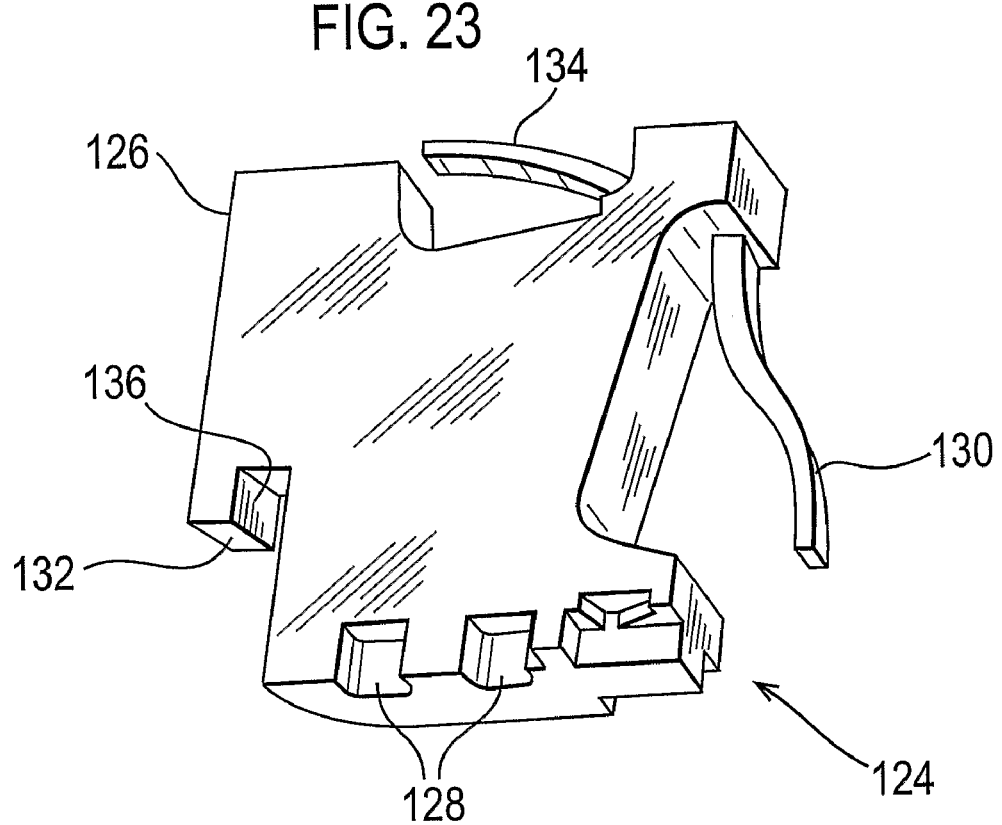
FIGS. 23 and 24 show opposing perspective views of the piston for the fault indicator of FIGS. 20 to 22.
Figure 24:
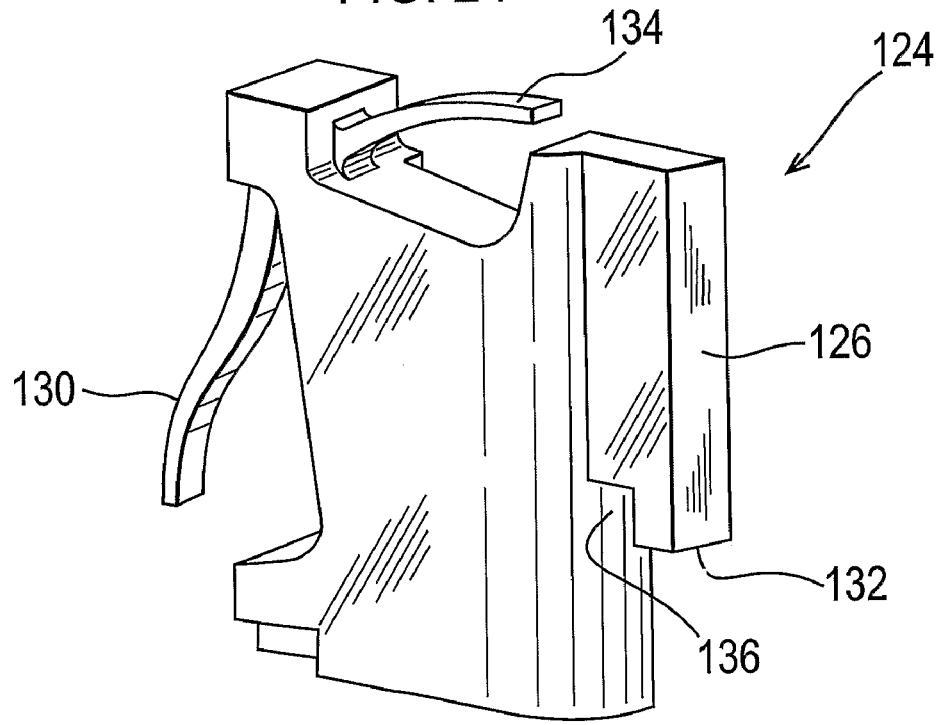

FIGS. 23 and 24 show a preferred piston for the fourth type of fault indicator. It comprises a toothed arrangement (128) at the bottom thereof and a strip bearing element (126) at the side thereof. Two resilient arms are also provided. The first resilient arm (130), which is integrally formed with the piston (124), is provided for providing a lateral bias for the piston (124). A second resilient arm (134), provided at the top of the piston (124), and also integrally formed, provides a downwards bias for the piston (124).

In use, the element (126) bears against the cover sheet (32) as the sheet passes around the nose portion (42). The cover sheet (32) holds the element (126) back in the nose portion (42) while there is no fault in the strip. However, upon a fault developing, the element (126) will spring outwards, i.e. move laterally. This will usually be by approximately 1 mm. It then will spring vertically downwards to engage the toothed arrangement (128) with the teeth (86) of the strip follower (26c).

The initial lateral motion allows the base (132) of the element (126) to clear the thin sidewall of the nose portion (42). The first resilient arm (130) bears against a rear sidewall of the nose portion (42) to provide the bias for this motion. The second resilient arm, however, bears against a fixed member above it, perhaps the underside of the top wall of the nose portion (42), to cause the second, downward, movement. The downward motion engages the side wall of the nose portion (42) into a slot (136) provided behind the element (126).

Preferably the second resilient arm (134) is in registration with a hole (142) at the top of the nose portion (42). The fixed member for the resilient arm to bear against can then be a depending flange (not shown) in the top half of the cover of the inhaler. Then, only upon fully assembling the inhaler will the second resilient arm of the piston (124) be under compression. This facilitates the assembly of the inhaler.

Figure 25:
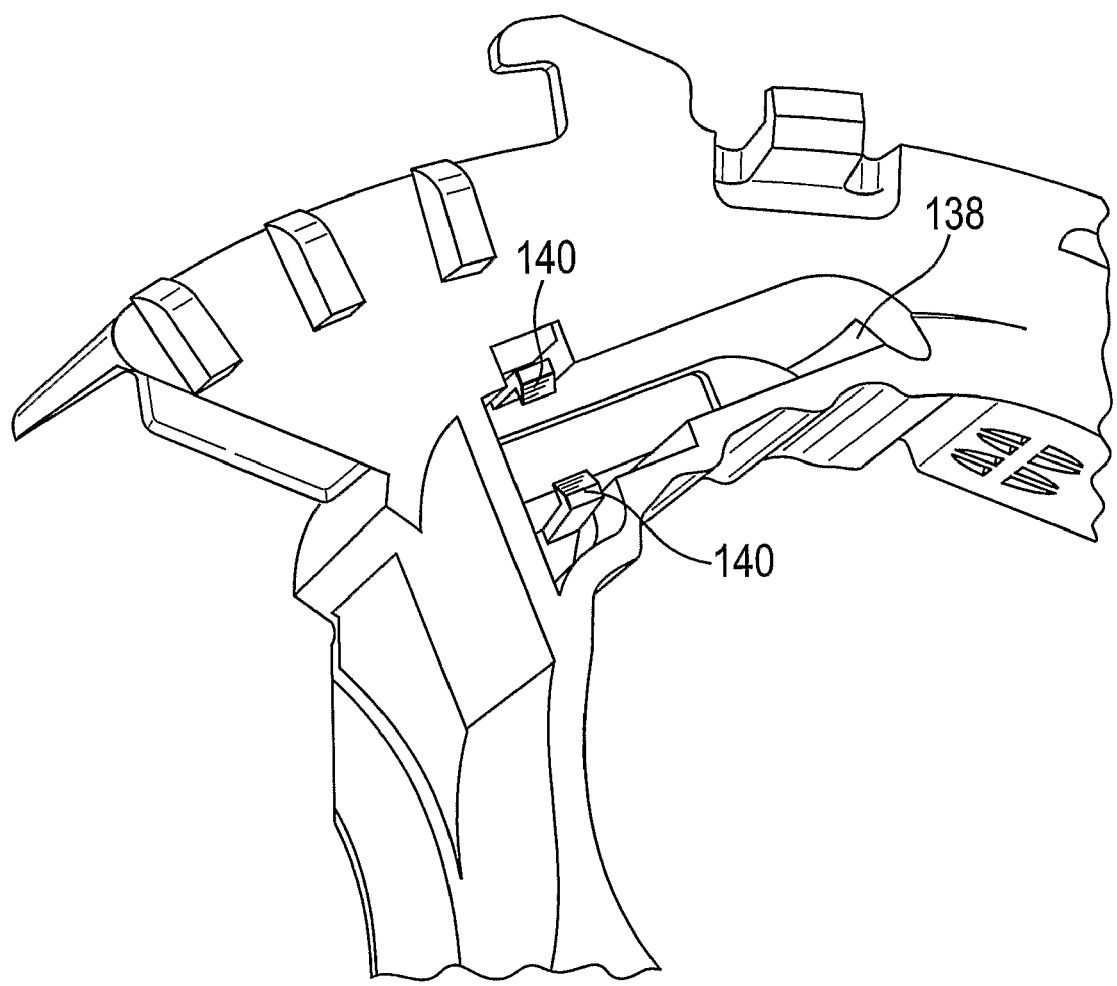
FIG. 25 is an underneath view of the manifold or base for receiving the piston of FIGS. 23 and 24.

Referring now to FIG. 25, an underside of the manifold for receiving the piston (124) of this fourth embodiment is shown. The underside comprises a slot (138) for receiving the piston (124) and two resilient clips (140) for locking the piston (124) in the slot (138). The clips (140) have inwardly extending flanges for engaging the underside of the piston (124) but tapered leading faces to allow the insertion of the piston (124).

Figure 26:
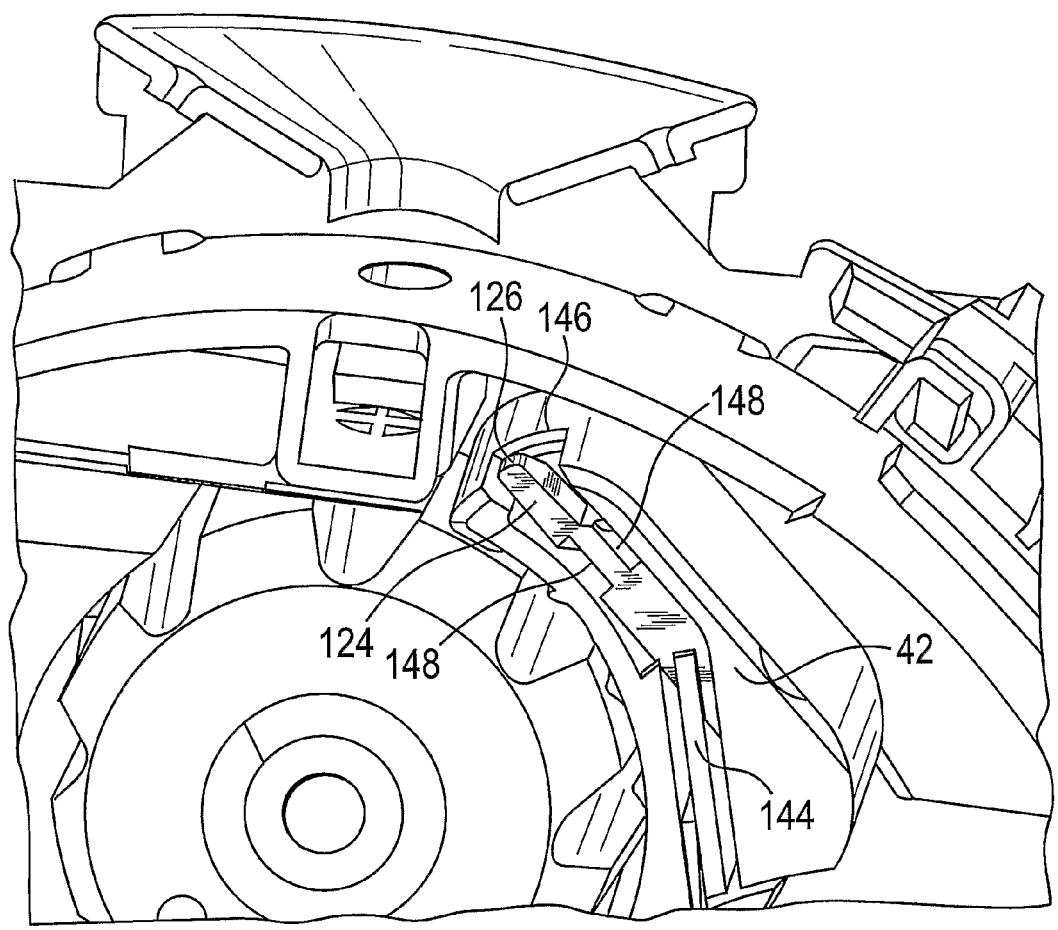
FIG. 26 shows a further embodiment of fault indicator in accordance with the present invention.

Referring now to FIG. 26, a variant of the fourth type of fault indicator is shown. It again comprises a piston (124) with an element (126) for bearing against a cover sheet (32) as it passes along the path to the lead spool (26a) via the nose portion (42). Further, the element (126) is adapted to extend laterally out of the end of the nose portion (42). However, instead of having two resilient arms (130,134), the second resilient arm is replaced with a resilient arm (144) integrally formed in the top wall of the nose portion.

In use, the piston (124) will be biased against the cover sheet (32), with the tension in the cover sheet (32) holding the piston in its non-fault position. However, if the foil breaks, or if it is not present, the piston will move to a fault indicating position laterally forward and vertically downwards from its non-fault position to bring the toothed arrangement (128) at the bottom of the piston into engagement with the teeth (86) of the guide pulley (26c).

Preferably the motion of the piston involves a 2.4 mm forward motion and a 1.5 mm downward motion.

Figure 27:
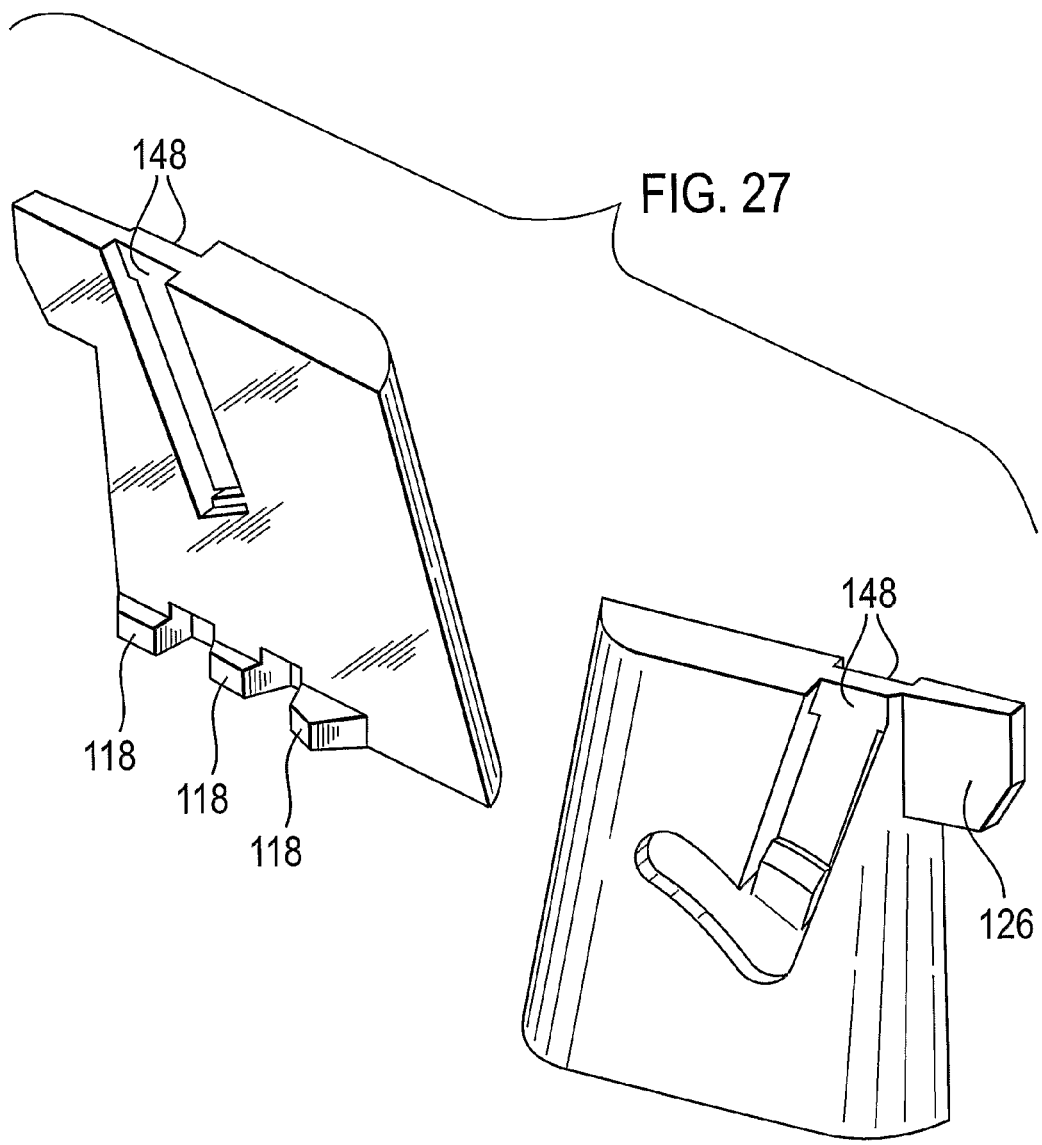
FIG. 27 shows opposing perspective views of an alternative piston for a fault indicator.

A further variant is shown in FIG. 27. In the sides of this piston (124), two straight and diagonal guide slots (148) are provided. Support pins or bars (not shown) are provided in the manifold to extend into these slots so as to guide the piston as it slides between its non-fault position and its fault indicating position. As before, the cover sheet will hold the piston (124) in a non fault position until a fault is to be indicated. For indicating the fault, the piston moves laterally and vertical to enable its engagement with the gear train.

The teeth of the toothed arrangement (118) extend sideways out from the piston wall in this embodiment for engaging the teeth (86) of the guide pulley (26c).

Preferably in the non-engaged position, the toothed arrangement hooks underneath the teeth (86) of the guide pulley (26c) so that, upon triggering the piston to move upwards, the teeth of the toothed arrangement (118) will come up to mesh with the teeth (86) of the guide pulley (26c).

Instead of first moving forward and then moving upwards or downwards, a piston might be provided to slide diagonally. The movement direction will be dependant upon the design, and in particular the direction of any slant of any guide slots, and their interactions with support pins or bars provided therefor (the pins may, for example, be in the piston, and the slots in the manifold).

A biasing member (not shown) may be arranged above or underneath the piston to bias it into its fault indicating position. Alternatively, the upward or downward thrust may be provided by the slots (148) interacting with the support pins or bars, transferring lateral thrust into an upward or downward thrust. Then, the piston could be provided with just a lateral biasing member (not shown).

Figure 28:
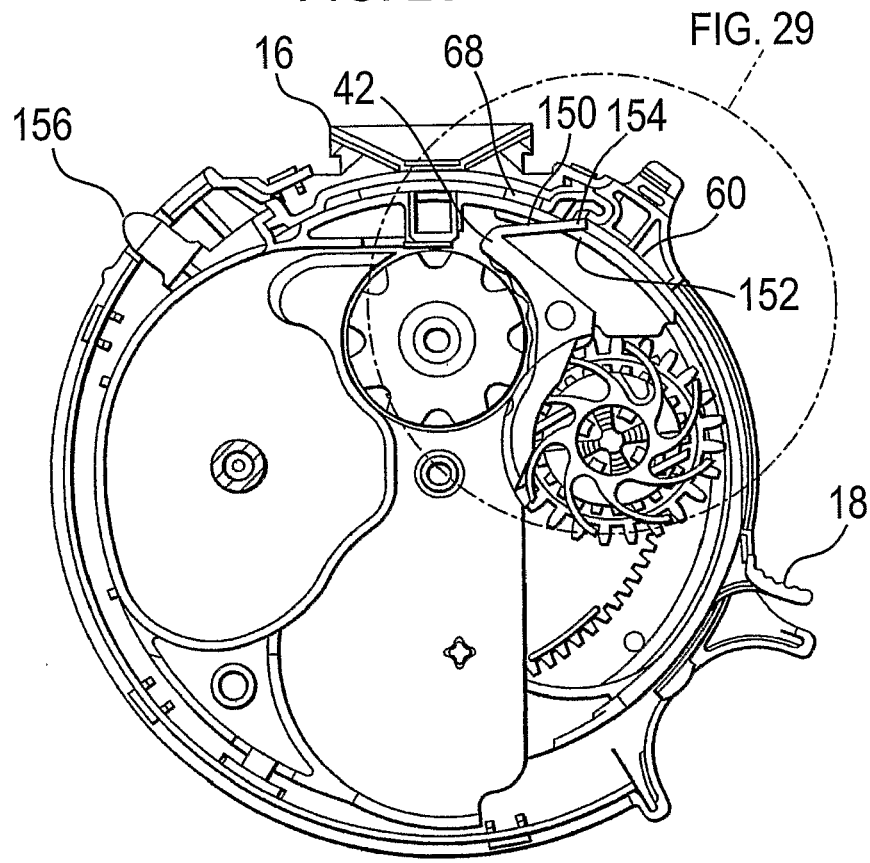
FIG. 28 is a plan view of a further embodiment of the present invention.

Referring now to FIG. 28, a further embodiment of the present invention is shown. This device, like the previous devices, comprises a nose portion or beak (42). However, a resilient arm (150) is formed onto the nose portion (42).

Figure 29:
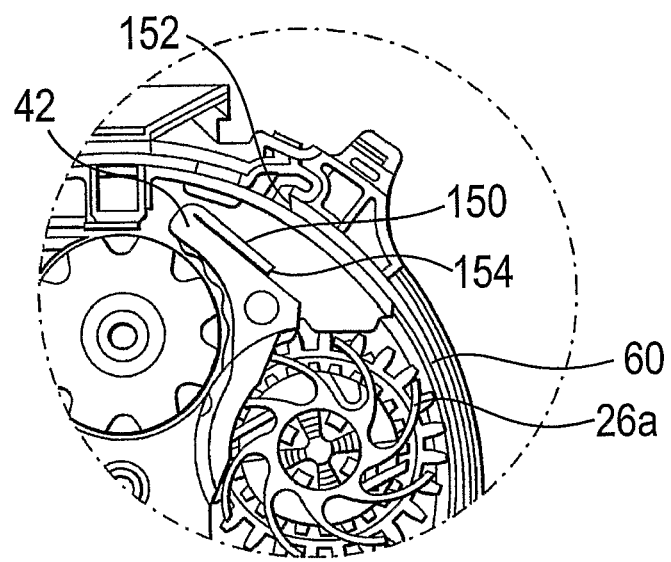
FIG. 29 shows a more detailed view of the fault indicator of FIG. 28 in a non-fault position.

In FIG. 28, the resilient arm (150) extends away from a side wall of the nose portion (42). This is the fault indicating position for the resilient arm. However, in FIG. 29, a more detailed view of part of the device of FIG. 28, the resilient arm (150) lies against the side wall of the nose portion (42). This is the non-fault position. The resilient arm (150) is resiliently biased to its fault indication position by virtue of it being integrally formed with the nose portion (42).

In normal use, the cover sheet (not shown) will pass along a generally similar path to that previously described, i.e. passing from a source spool, around various sides of the nose portion (42) and then onto a lead spool (26a) for winding up the cover sheet (32). By following this path, the tension in the cover sheet will cause the resilient arm (150) to be held in its non-fault position, i.e. against the nose portion (42). However, should the strip (22) or cover sheet (32) slacken, break, tear, stretch or fail, then the tension in the cover sheet (32) would be lost and the resilience of the resilient arm (150) would cause the arm (150) to spring outwardly towards its fault indicating position, as shown in FIG. 28.

In the fault indicating position, the distal or free end (154) of the resilient arm (150) could simply provide a visual indicator of a fault, for example by the device being provided with a suitably placed window in the outer casing, i.e. for seeing the resilient arm when it has moved to its fault indicating position. However, in this embodiment, the resilient arm operates as a blocking means, thereby providing a strip advancement lock-out—it blocks the trigger (18).

As can be seen in FIG. 28, the trigger (18) is in its trigger advanced position (corresponding to FIG. 2). As a result, the groove follower (60) is also fully advanced clockwise (as shown). In this fully advanced position, the free end (152) of the groove follower (60) moves beyond registration with the free end (154) of the resilient arm (150). As a result, the free end (154) of the resilient arm will spring outwardly into the groove (68) provided for the groove follower (60). Then, upon releasing the trigger (18), the free end (152) of the groove follower (60) would be blocked by the free end (154) of the resilient arm (150). This would prevent the return of the trigger (18) to its default position.

The length of the resilient arm (150) is longer than the width of the gap between the arm's non-free end and an outer side wall of the groove (68). This is so that the free end (154) of the resilient arm (150) engages the outer side wall of the groove (68) before the resilient arm becomes perpendicular to that side wall. With this arrangement, attempts to move the trigger to its default position by forcing it against the arm (150), when the arm (150) is in its blocking position, will simply cause the resilient arm (150) to bear against the side wall of the groove (68). It will therefore resist the forcing.

Instead of forming the resilient arm integrally within the nose portion (42), the resilient arm (150) could be replaced with a hinged arm that is biased to a fault indicating position by a spring.

The resilient arm forms the element for bearing against the strip or component thereof.

Instead of the resilient arm bearing against the free end (152) of the groove follower when it is in its fault indicating, or blocking, position, the groove follower (60) may be provided with a recess (70) (as per FIG. 3) for receiving the free end (154) of the resilient arm (150).

The device of FIG. 28 is also shown to comprise an LED (156). This LED (156) could be wired to a switch and an electrical circuit that is triggered as a result of the movement of the resilient arm for providing a further visual indicator of a fault.

Figure 30:
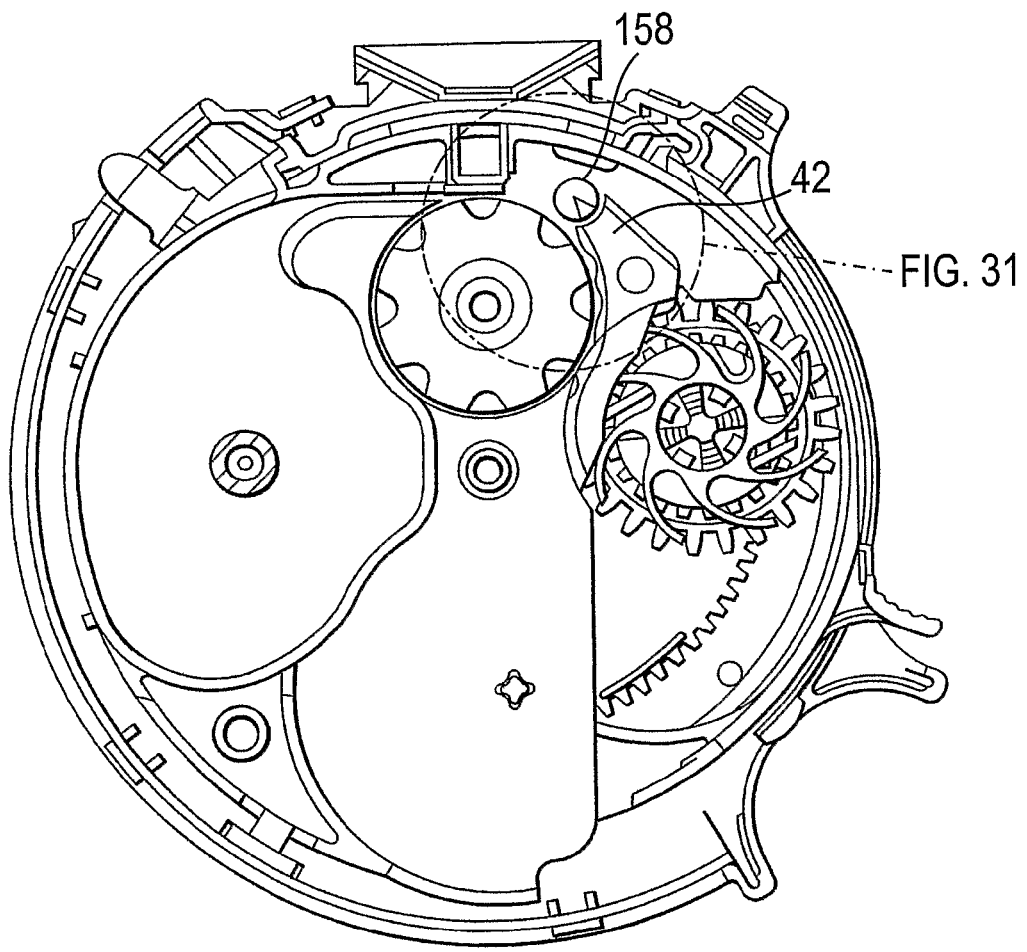
FIG. 30 shows a plan view of another embodiment of the present invention.
Figure 31:
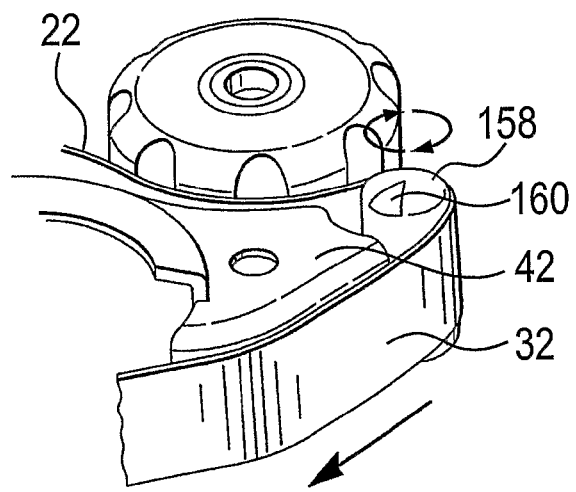
FIG. 31 shows a schematic perspective view of the fault indicator of FIG. 30.

Referring now to FIGS. 30 and 31, another embodiment of the present invention is disclosed. It comprises a device that is similar to that disclosed in FIGS. 28 and 29. However, in place of the resilient arm, there is provided a rotating element (158). It forms a rotating tip for the nose portion (42). The rotating element is shown more clearly in the perspective view of FIG. 31.

The rotating element (158) comprises a cylinder that is mounted on a manifold or base of the device for rotation about an axis that extends perpendicular to the path of the strip (22) and the top and bottom halves (12, 14) of the clam shell case for the device.

The cover sheet (32) follows a path around the rotating element (158). As shown in FIG. 31, as the cover sheet (32) of the strip (22) passes around the rotating element (158), the rotating element (158) rotates with it since the cover sheet (32) bears against the rotating element. This is due to the tension in the cover sheet (32) caused by the lead spool (26a) winding up the cover sheet (32).

An indicia (160) is provided at the top of the rotating element (158). This indicia (160) is a brightly coloured marker or an upstanding pointer. As the rotating element (158) rotates, the indicia (160) will rotate. A window (not shown) is positioned in the top half of the clam shell case of the device for viewing the top of the rotating element (158).

If there is no fault in the cover sheet, then the rotation of the rotating element (158) will be readily observable by casual observation through the window as the sheet advances. However, upon a fault developing in the cover sheet (32), the tension will be lost in the cover sheet (32). Therefore, the cover sheet will no longer cause the rotating element (158) to rotate. Therefore, a visual indication of a fault would be provided to a user by him noting through the window that the indicia at the top of the rotating element (158) is not rotating as the trigger is advanced.

If desired, the window may be positioned so that it is possible to observe the rotation when inhaling through the mouthpiece (16).

The indicia has no degrees of rotational symmetry—from above it is a neutral or white circle provided with a coloured (red) segment or sector. Accordingly, casual observation through the window either upon trigger advancement, or upon observation of the indicia both before and after trigger advancement, will readily determine whether it is rotating.

Alternative indicia can be provided, but rotation of the rotating element (158) must readily be observable by a user, so indicia having three or less degrees of rotational symmetry are preferred.

Referring now to FIGS. 32 to 35, another embodiment of the present invention is disclosed. This embodiment uses a resilient post (162) as its element. The post (162) is adapted, in use, to bear against the cover sheet (32) as it passes between the nose portion (42) and its lead spool (26a). It has a smooth sheet-bearing surface, in this embodiment formed by the post (162) having a circular cross section.

The post (162) extends across the path of the cover sheet (32), perpendicular to the direction of movement of the cover sheet (32) and the two halves of the clam shell case for the device.

Figure 34:
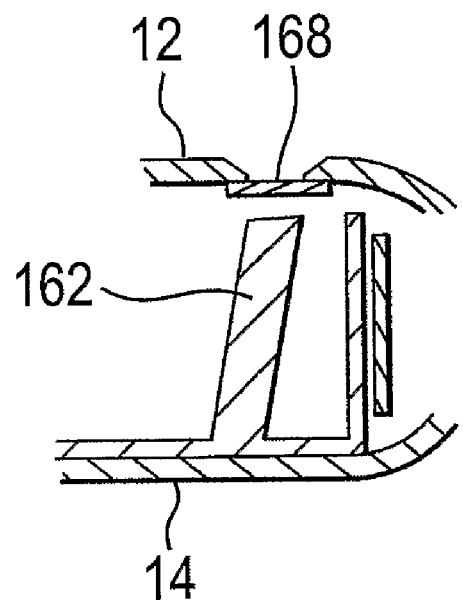
FIG. 34 is a schematic view of the fault indicator of FIG. 32 in a fault indicating position.
Figure 35:
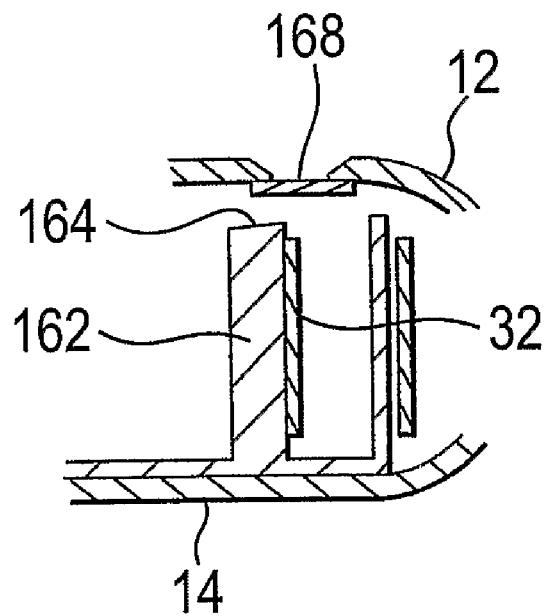
FIG. 35 shows the same fault indicator as FIG. 34, but in a non-fault position.

As shown in FIGS. 34 and 35, the resilient post (162) is biased from a non-fault position, as shown in FIG. 35, into a fault indicating position, as shown in FIG. 34. It can be held in its upright, non-fault position, as shown in FIG. 35, by tension in the cover sheet (32) as the cover sheet (32) passes over the post (162).

Figure 33:
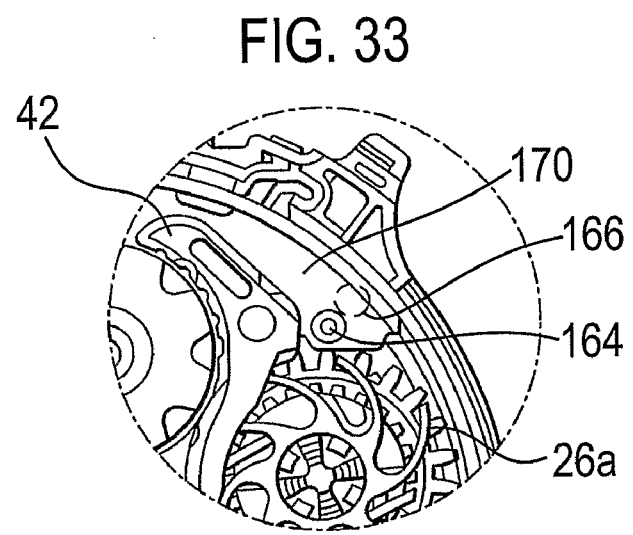
FIG. 33 shows more details of the embodiment of FIG. 32 with the fault indicator in a non-fault position.

FIG. 33 is a view from above which shows the end (164) of the post in its non-fault position. It has a coloured (red) marker or dot on its top surface. Other indicia are possible, however. FIG. 33 also shows, in dotted line (166), the fault indicating position for the end (164) of the post (162) if it was to be released into its fault indicating position. The indicia at the end (164) of the post (162) is provided for moving into registration with a window (168) provided in the top half of the clam shell case as the post moves into its fault indicating position to notify the user that there is a problem. However, in the non fault position, the indicia is not visible through the window (168).

An advantage of this system is that it is easy to retrofit into a prior art inhaler. The post (162) can be mounted on a base plate (170) that can be glued to the bottom half (14) of the clam shell case in an appropriate position for the post to bear against the cover sheet (32). Further, the window can be formed in the case simply by drilling a hole through the top half (12) of the case and then gluing a clear plastic window over the hole for closing the hole to prevent dust ingress into the device.

In an unillustrated modification to the embodiment of FIGS. 32 to 35, the post (162) is located on the outer side (relative to the device) of the cover sheet (32) and biased inwardly towards the gearing (26b) of the lead spool (26a), but is restrained by the outer face of the cover sheet (32) in the non-fault condition. In the event of a tear forming in the cover sheet (32), the post (162) springs inwardly when there is no longer any cover sheet (32) to resist the inward movement. The post (162) in this embodiment would be provided with some feature to engage the gearing (26b) to block further rotation thereof on next operation of the trigger (18), thereby indicating to the user the failure in the device. For instance, the inner surface of the post could be given a tooth arrangement. It will therefore be appreciated that the window (168), suitably relocated to register with the fault indicating position of the post (162), would give a supplemental visual fault indication. However, the window (168) could, of course, be dispensed with.

In another unillustrated embodiment, instead of the post (162) being located on the outer side (relative to the device) of the cover sheet (32), another fault indicator could be used comprising a spring member which biases the fault indicator inwardly so as to bear against the outer face of the cover sheet (32) when no fault is present. However, if there is no cover sheet (32) to resist the inward bias of the fault indicator, such as after a tear is formed in the cover sheet (32), the fault indicator moves inwardly to a fault indicating position in which the fault indicator is wedged between the intermeshing gearing (26b) of the lead spool (26a) and the gearing (86) of the guide pulley (26c)—see FIG. 8 which shows the gearing (86) of the guide pulley (26c). The fault indicator could be provided with an inwardly-facing end having a wedge-shaped, toothed or "Christmas tree" profile.

In a further unillustrated embodiment, a fault indicator is provided formed of two parts, a sliding latch part which is biased (e.g. by a spring element) outwardly (relative to the device) against the inner face of the cover sheet (32), for restraint by the cover sheet (32) as in the other embodiments, and a post part which is arranged for movement parallel to the plane of the cover sheet (32) and generally perpendicular to the direction of outward bias of the latch part. The post part may be biased to its fault indicating position, e.g. with a spring element. In the non-fault condition, the latch part bears against the inner face of the cover sheet (32) and the post part is latched by the latch part in a non-fault indicating position, e.g. by the latch part inter-engaging with the post part, e.g. an enlarged end of the post part. If the cover sheet (32) fails to resist the outward movement of the latch part, e.g. due to a tear forming in the cover sheet (32), the latch part slides outwardly therefore unlatching the post part enabling the post part to move to a fault indicating position. In its fault indicating position, the post part may provide a visual indication, e.g. in a window or aperture in the device casing, and/or block the strip advancement mechanism against further operation, e.g. by meshing with a gearing of the strip advancement mechanism, for instance the gearing (86) of the guide pulley (26c). In the latter instance, the post part may have a blocking end of a toothed profile.

Figure 36:
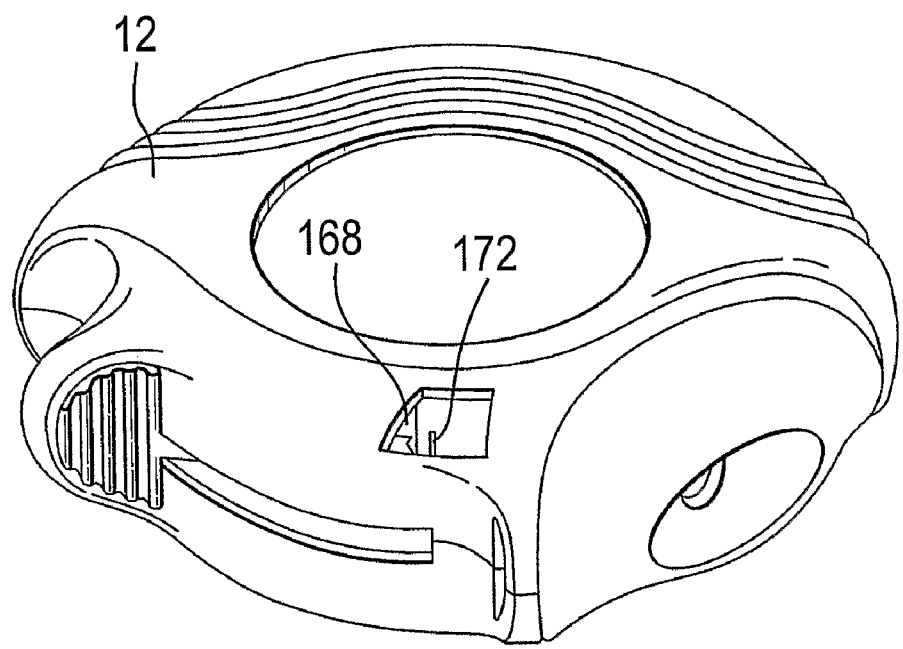
FIG. 36 shows a further embodiment of the present invention having a window for viewing a fault indicator.
Figure 37:
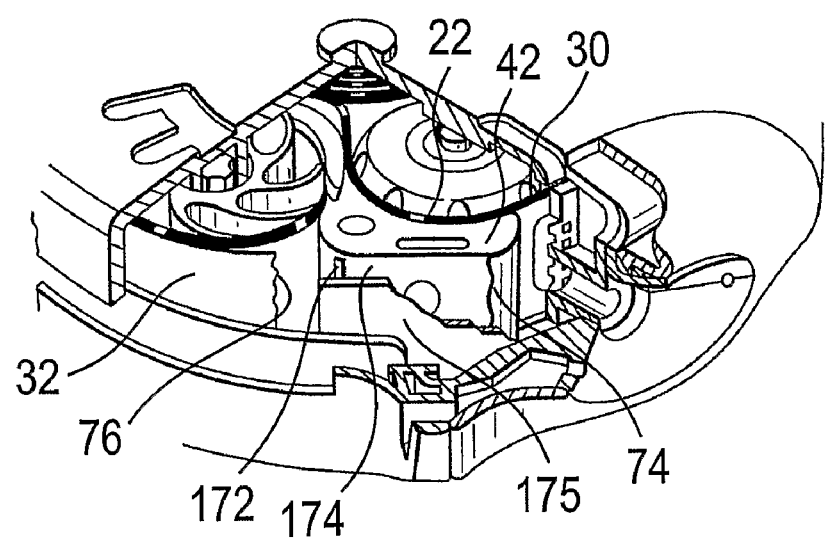
FIG. 37 is a cutaway, more detailed view of the embodiment of FIG. 36.
Figure 38:
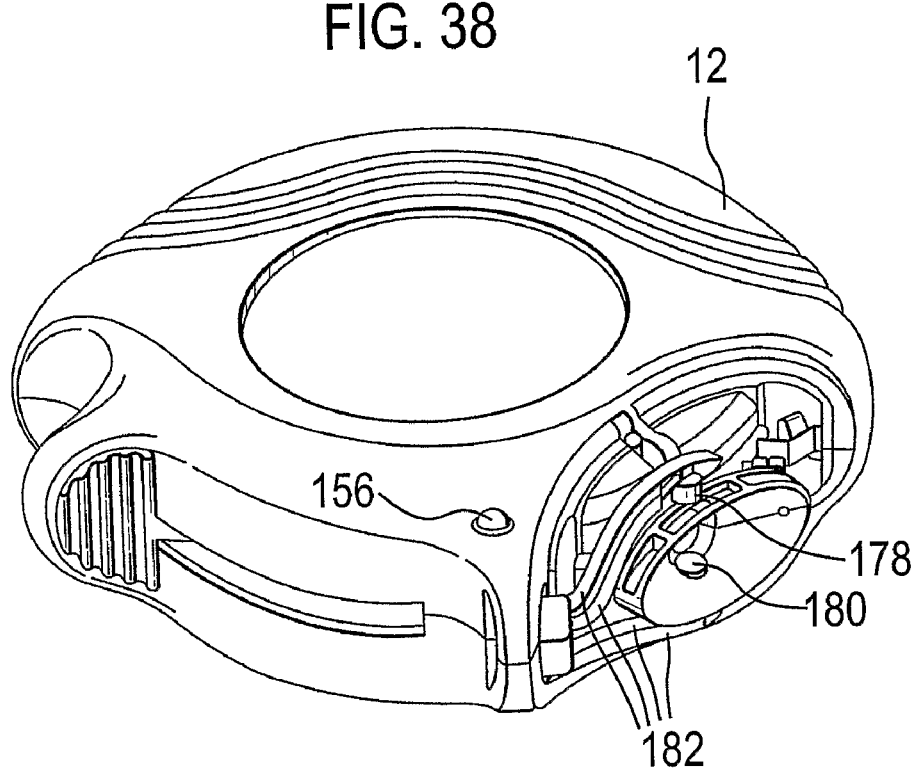
FIG. 38 shows a further embodiment of the present invention with a protective shroud removed.
Figure 39:
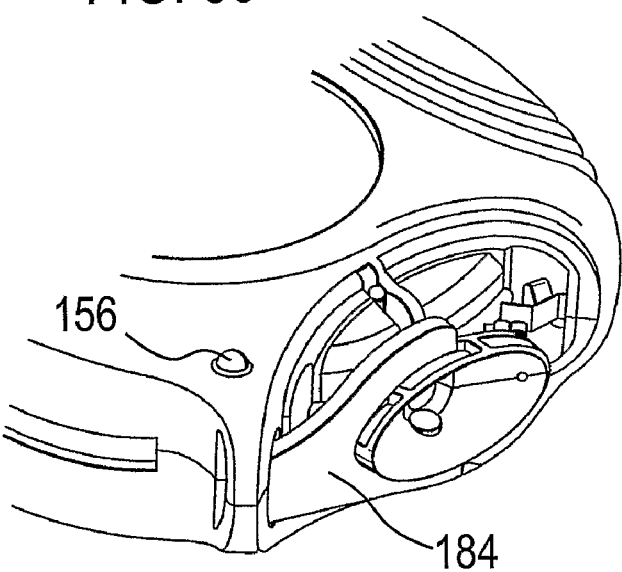
FIG. 39 shows the embodiment of FIG. 38, but with the protective shroud present.

Referring now to FIGS. 36 and 37, another embodiment of the present invention is disclosed. In this embodiment, a window (168) is provided in the top half (12) of the clam shell case. The window (168) is similar to that which might have been provided in previously disclosed embodiments, and is again for visualisation of a fault indicator (172). The fault indicator (172), however, is a coloured indicia (a red line) provided on a guide surface (174) for the cover sheet (32). The guide surface is part of a side wall of the nose portion (42).

The fault indicator (172) is positioned on the guide surface (174) such that the cover sheet (32) will cover it when the cover sheet (32) runs along its normal path, i.e. so that the fault indicator (172) will not be visible. However, upon the cover sheet (32) slackening, breaking, tearing, stretching or failing, the resulting free end (76) of the cover sheet (32) will be wound up onto the lead spoon (26a), thereby passing clear of the fault indicator (172) to reveal the fault indicator (172). The use will then be able to see the fault indicator (172) through the window (168). Although a coloured line is shown, other indicia could be provided for visualisation through the window (168) upon the cover sheet (32) slackening, breaking, tearing, stretching or failing.

Opposite the guide surface (174) of the nose portion (42), a second guide surface (175) is provided. It is spaced a small distance away from the first guide surface (174) for defining a guide channel therebetween. The cover sheet (32) passes through the guide channel to ensure that the cover sheet (32) is maintained in its position over the fault indicator (172) if the coversheet (32) slackens only slightly, for example due to any slight stretching of the cover sheet (32), but not the base sheet (30). The second guide surface, however, is not essential.

The second guide surface (175) has a shorter height than the first guide surface (174) so that it will not obscure the visibility of the fault indicator (172) through the window (168).

The window in the top half (12) of the clam shell case can also be used for observing the advancement of the cover sheet (32), irrespective of whether there is a fault. This can be a comfort for the user.

Referring now to FIGS. 38 to 41, a further embodiment of the present invention is disclosed. In this embodiment, the device is an inhaler having a mouthpiece (16). A light emitter and sensor arrangement for detecting faults is fitted to the inhaler, for passing a beam of light across the lumen (176) of the mouthpiece (16). Further, an LED (156), connected to the light emitter and sensor arrangement, is provided adjacent the mouthpiece (16) for indicating whether a fault has been detected by the light emitter and sensor arrangement.

Figure 32:
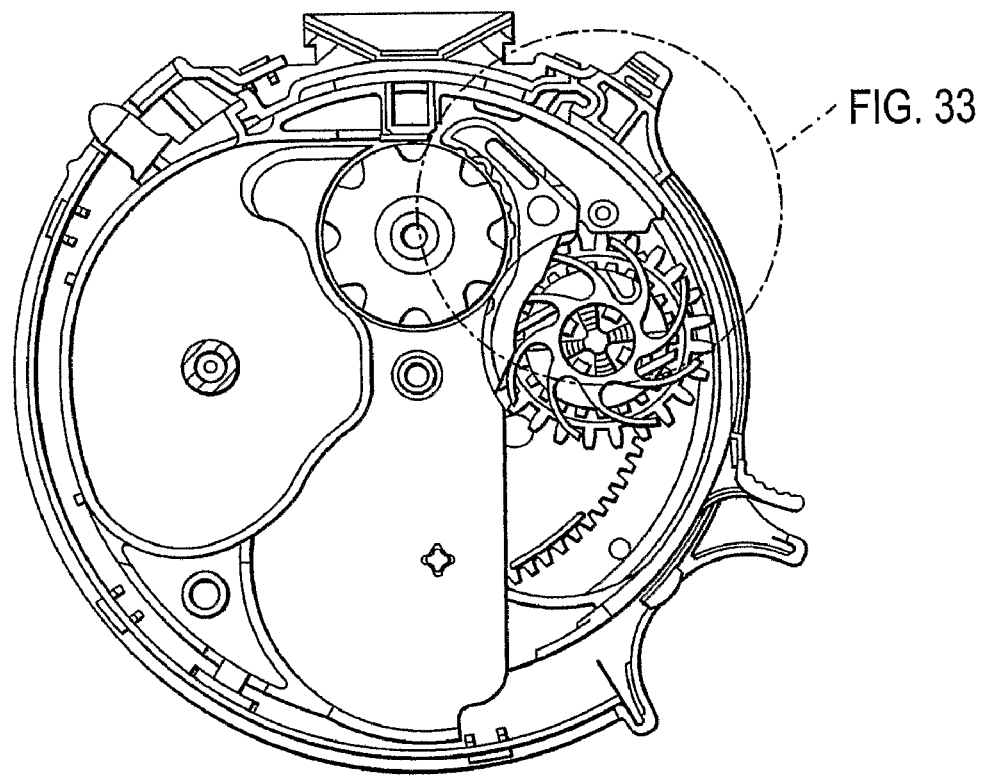
FIG. 32 shows a plan view of another embodiment of the present invention.

Whereas in FIGS. 28, 30 and 32, an LED (156) is shown to be in a side of the device, in this embodiment, the LED (156) is positioned in the top half (12) of the clam shell case, i.e. towards an opposite side of the mouthpiece (16) compared to those other embodiments. The LEDs in those other embodiments may be connected to a system as about to be described, rather than to some other system.

The light emitter and sensor arrangement comprises a light emitter (178) and a light sensor (180). They are provided on diametrically opposed sides of the lumen (176) of the mouthpiece (16) so that light can be emitted by the emitter (178) across the lumen (176) to the sensor (180). Wires (182) for both the light emitter (178) and the light sensor (180), connecting them to a power supply (not shown), an optional controller (not shown) and the LED (156), extend from the light emitter and the light sensor. They are usually covered by a protective shroud (184) (see FIG. 39). The shroud (184) preferably forms a seal over the wires (182) to protect them from powder or moisture ingress due to inhalation of medicament from the strip (22) through the mouthpiece (16).

Figure 40:
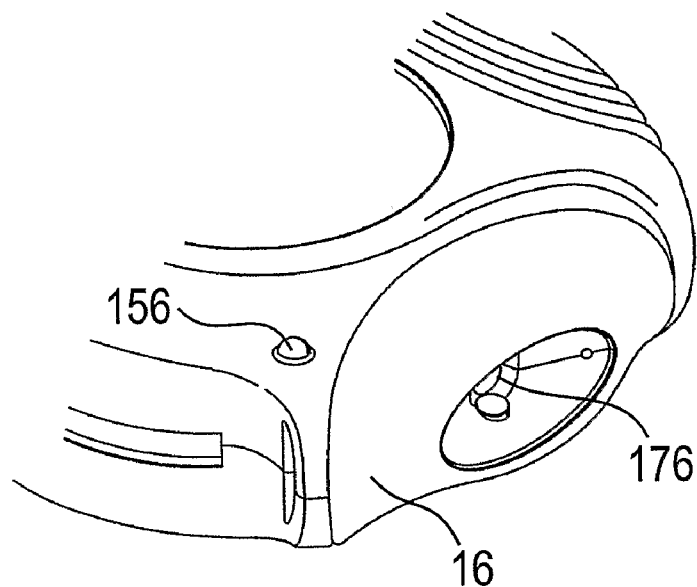
FIG. 40 corresponds with FIG. 39, but also has a mouthpiece fitted.

Over the shroud (184), the mouthpiece (16) is fitted—see FIG. 40. The mouthpiece (16) further encloses the light emitter and sensor arrangement.

Figure 41:
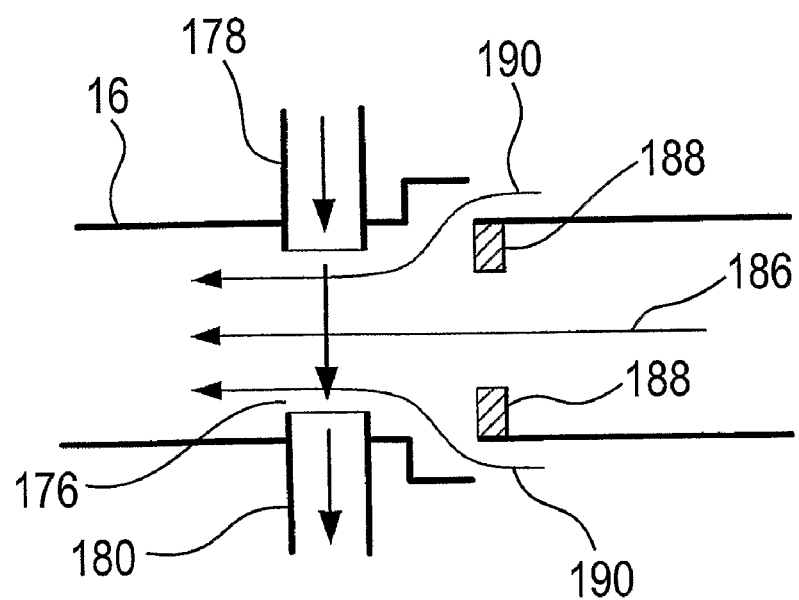
FIG. 41 is schematically shows the operation of the fault indicator in the device of FIG. 38.

Referring now to FIG. 41, the operation of the light emitter and sensor arrangement is shown schematically. The light emitter (178) fires a beam of light across the lumen (176) and this light is detected by the light sensor (180) provided on the other side of the lumen (176). When this light is detected the LED (156) will light up.

When a user inhales medicament through the mouth piece (16), the powder particles of the medicament from the strip will be entrained in the airflow. Therefore, they will pass through the lumen (176), as shown by the central arrow (186). The particles, therefore, will interrupt the light transmitted from the light emitter (178), thereby altering the amount of transmitted light sensed by the light sensor (180). Therefore, inhaling correctly, i.e. with a medicament flow, will cause the LED (156) to flicker. However, if there is no medicament in the airflow, then there will be no flickering of the LED (156). This non-flickering will alert the user to a problem.

In an alternative embodiment of this aspect of the invention, control circuitry can be provided and designed to only light up the LED (156) when there is no medicament flow through the lumen (176). This then provides a positive fault indication.

The light emitter and sensor arrangement preferably uses infra-red light.

A light guide can be used for the light emitter and/or for the light detector for transmitting the light either from the emitter (178) to the lumen (176) or to the sensor (180) from the lumen (176), so that the light emitter (178) and/or the light sensor (180) can be placed in a more protected position within the inhaler, i.e. deeper within the inhaler.

Still referring to FIG. 41, airflow buffers (188) are provided in the lumen (176) to direct the powder flow (186) and the airflow (190) through the lumen. The powder flow (186) is bounded by the airflow (190), thereby keeping it away from both the light emitter (178) and the light sensor (180) (or the light guides, if used). This reduces the amount of powder deposition that occurs on the surfaces of the light emitter (178) and the light sensor (180) (or the light guides).

Figure 42:
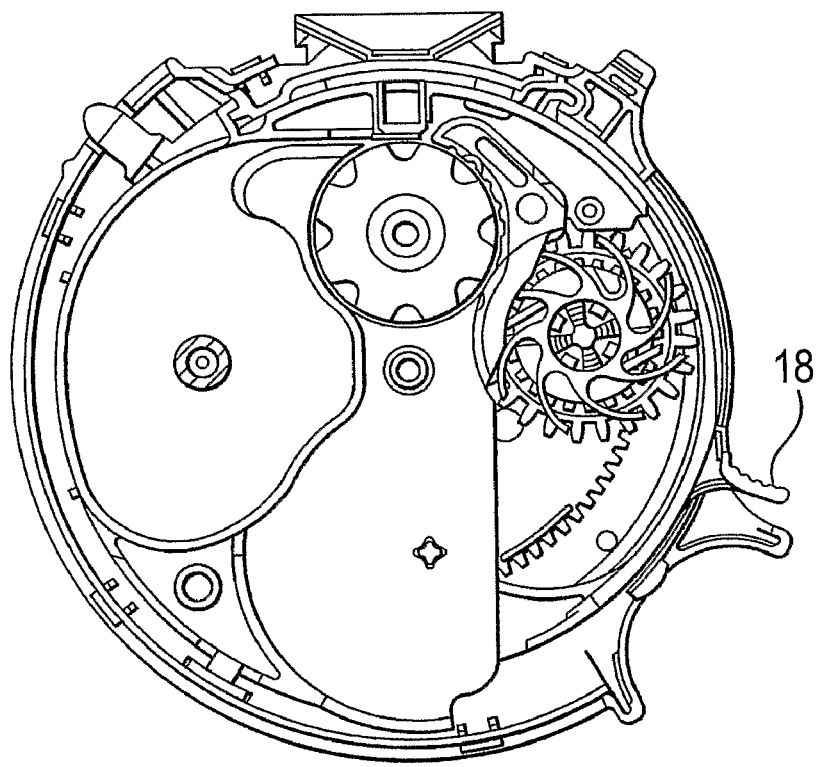
FIG. 42 is another embodiment of the present invention, having a clear or transparent trigger.
Figure 43:
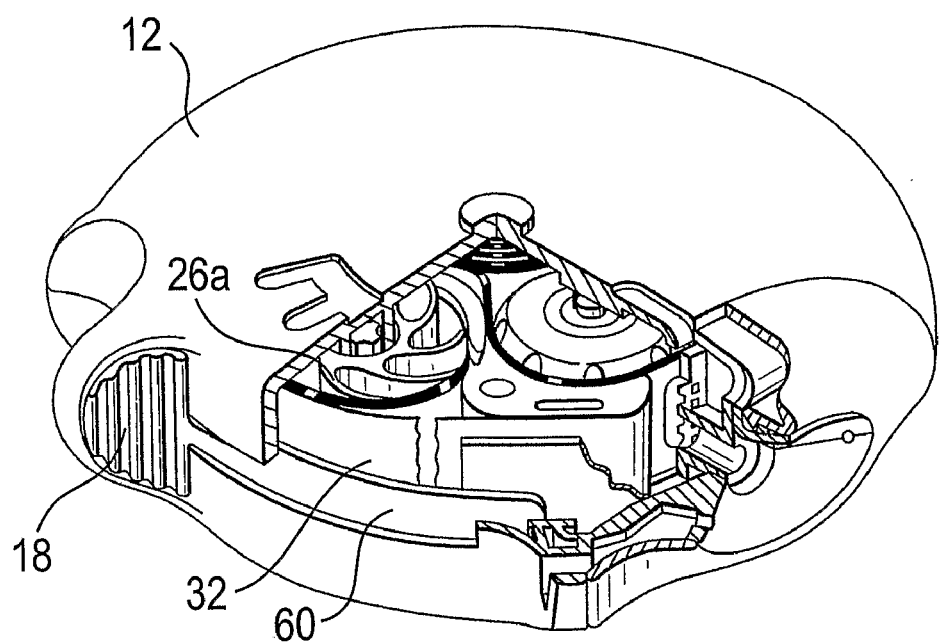
FIG. 43 shows a perspective cutaway view of the embodiment of FIG. 42.

Referring now to FIGS. 42 and 43, a further embodiment of the present invention is shown. In this embodiment, the trigger (18) is made of a clear plastics material (preferably polycarbonate—other clear or transparent materials could be used.

The clear trigger (18) is provided to allow the user to see into the device through the side of the device. Then, if the strip (22) has failed, the user would be able to see this by looking through the trigger (18) and looking at the cover sheet (32) as it is wound onto the lead spool (26a). A coloured indicia (e.g. a red line) could be provided on the guide surface (174) for the cover sheet (32), as described with reference to FIGS. 36 and 37. The indicia would be hidden by the cover sheet (32) in the no-fault condition, but would be visible through the clear trigger (18) in the event of strip failure. The clear trigger (18) may be provided in addition to other fault indicators, such as those described herein.

In another embodiment, a clear or transparent case could be provided for monitoring the internal mechanisms for verifying the functionality of the device.

Figure 45:
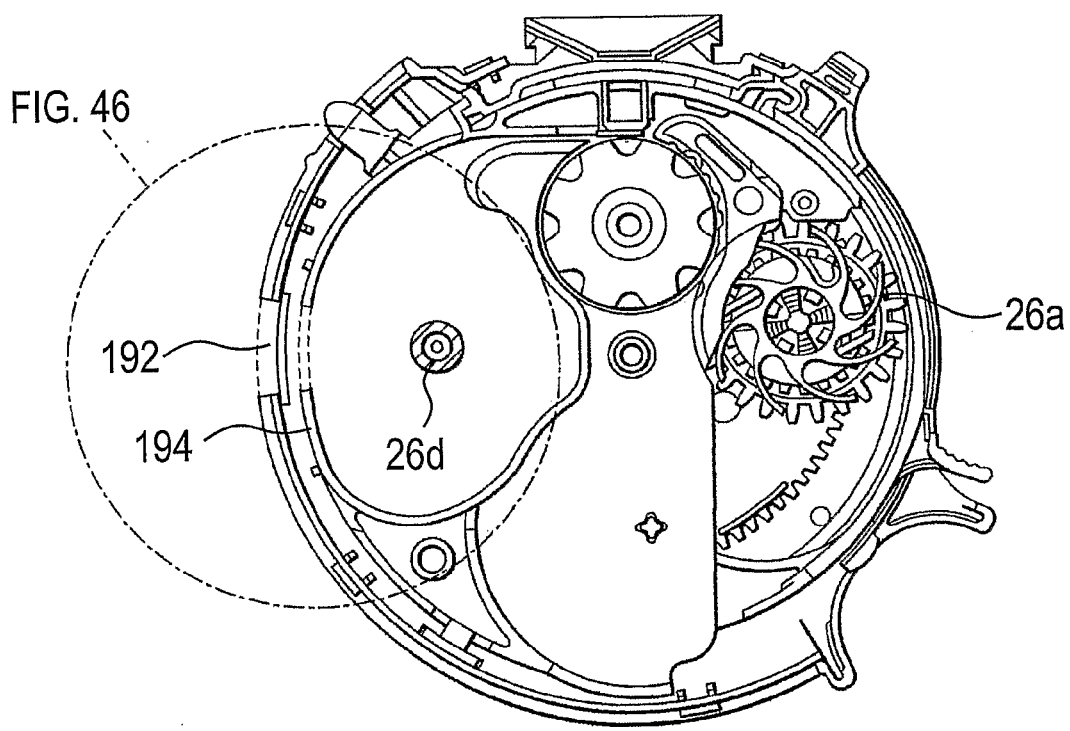
FIGS. 45 and 46 show yet another embodiment of the present invention.
Figure 46:
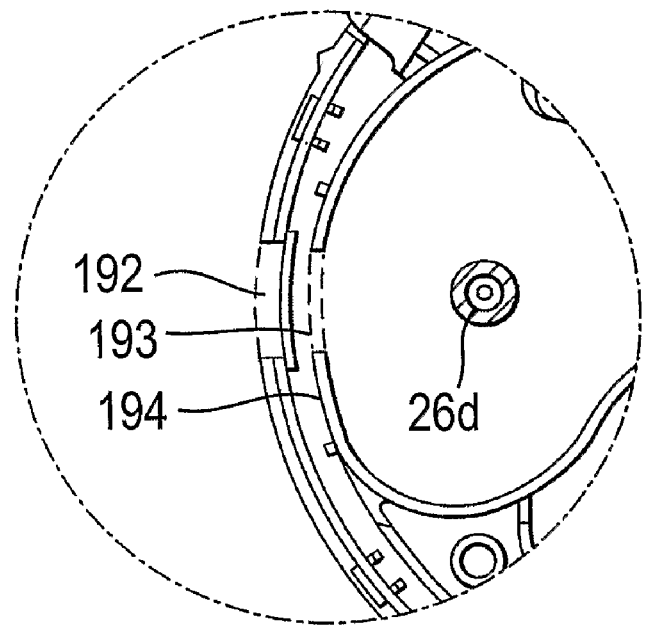
Figure 47:
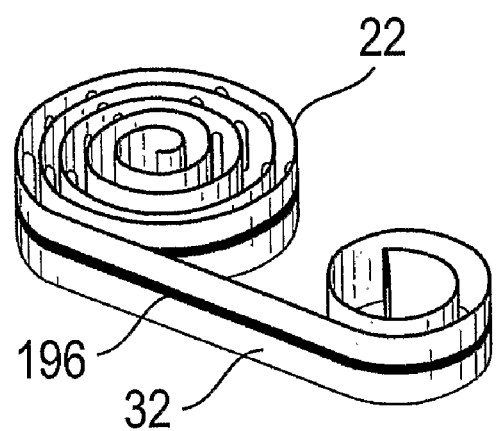
FIG. 47 shows a strip for use with the embodiment of FIGS. 46 and 47.

In yet another embodiment, as shown in FIGS. 45 and 46, a window (192) is provided in the side of the case, and in the side of an internal housing (194) for the second lead spool (26d), the two windows being in registration. These windows (192, 193) allow the winding of the base sheet (30), i.e. the sheet with the blisters (34, 36), onto its lead spool (26d), to be visualised for verification of correct winding thereof onto the lead spool (26d). For assisting this, as shown in FIG. 47, an indicator (196), such as a coloured (red) line, may be provided on the cover sheet (32). If the indicator (196) can be seen through the windows (192, 193) in the side walls of the case and housing (194), then the user will know that the cover sheet (32) has slackened, broken, torn, stretched or failed. The cover sheet (32) would otherwise be being wound onto the other lead spool (26a).

Figure 44:
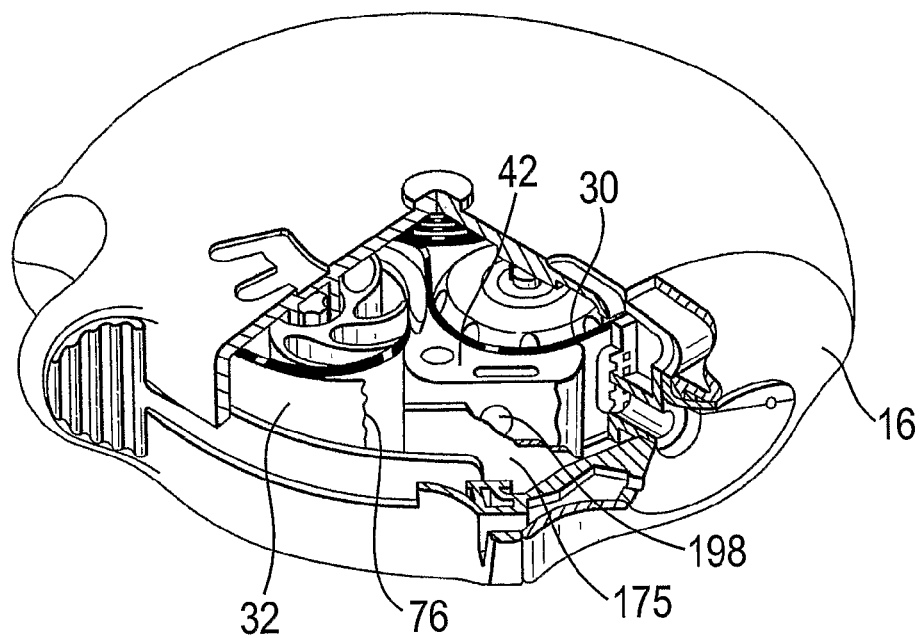
FIG. 44 shows a further embodiment of the present invention.

Referring finally to FIG. 44, another embodiment of the present invention is shown. In this device, an audible fault indicator is provided in the form of a whistle hole (198). The whistle hole (198) is provided in a guide surface for the strip (22)—in a side wall of the nose portion (42).

In normal use, the whistle hole (198) will be covered by the cover sheet (32). However, FIG. 44 shows a broken cover sheet (32). Further, the free end (76) of the cover sheet (32) has moved past the whistle hole (198) so the whistle hole (198) is open. Therefore, any subsequent inhalation through the mouthpiece (16) will cause airflow to pass through the device and over the whistle hole (198). That airflow will cause the whistle hole (198) to whistle. This whistling noise will alert the user to a fault in the device. However, if the hole was to be covered by the strip (22), then the hole would be closed, thereby not whistling.

The whistle hole (198) can be provided elsewhere in the device, but it must be covered when the strip is intact. This should usually be done by the strip (or a component thereof) when the strip (or the component thereof) follows its normal path through the device.

The whistle hole (198) is positioned adjacent to or near the mouthpiece (16) so that the airflow is strong as it passes the whistle hole (198).

As with the embodiment of FIG. 37, this embodiment uses a second guide surface (175) for maintaining the cover sheet (32) in its correct path as it passes the fault indicator, the whistle hole (198), i.e. the cover sheet (32) is in the groove channel. Further, the second guide surface is not as tall as the first guide surface. This is so that it does not cover the whistle hole (198). If it was to cover the whistle hole (198), the whistle hole (198) would not ever whistle.

The above embodiments provide numerous ways in which to provide a fault indicator for an inhaler, or simply for a strip advancement mechanism, by means of which a fault can be indicated to the user by visual, tactile, audible or other means.

In those embodiments described above which utilise a fault indicator element which bears against the cover sheet (32) of the strip (22) in the non-fault condition, it will be appreciated that any flaw in the cover sheet (32) which results in a loss in tension in the cover sheet (32), such as a tear, may allow the fault indicator element to move to its fault indicating position while the cover sheet (32) is still in front of the fault indicator element (i.e. in the fault sensing path), since the tension in the cover sheet (32) is no longer sufficient to restrain the biasing force from biasing the fault indicator element to the fault indicating position. In other words, it may not be necessary for a torn-off or severed section of the cover sheet (32) to go past the fault indicator element for the fault indicator element to move to its fault indicating position.

The present invention has been described above purely by way of example. It should be noted, however, that modifications in detail may be made within the scope of the invention as defined in the claims appended hereto.

What is claimed is:

1. An inhaler comprising a strip containing a medicament, a strip advancement mechanism for advancing the strip through the inhaler and a fault indicator comprising a base that defines a fault sensing portion of a path for at least a component of the strip, an element for bearing against the strip, or a component of the strip, while it passes through the fault sensing portion of the path, and wherein the element is adapted to move from that bearing or non-fault position, to a fault indicating position in the event of the strip or the component of the strip ceasing to pass through the fault sensing portion of the path.

2. The inhaler of claim 1, wherein the element is biased to the fault indicating position.

3. The inhaler of claim 1, comprising a strip advancement lock-out mechanism.

4. The inhaler of claim 3, wherein the strip advancement lock-out mechanism comprises a blocking member that, upon the element moving into the fault indicating position, blocks further actuation of the strip advancement mechanism.

5. The inhaler of claim 4, wherein the element comprises the blocking member.

6. The inhaler of claim 4, wherein the blocking member comprises a toothed section for lockingly engaging gear teeth of a gear in the strip advancement mechanism.

7. The inhaler of claim 4, wherein the blocking member is adapted to block movement of a manually-operated trigger of the strip advancement mechanism.

8. The inhaler of claim 1, wherein the element is biased by a spring to the fault indicating position.

9. The inhaler of claim 1, wherein the element is in the form of a piston element or a rotatable lever element.

10. The inhaler of claim 1, wherein the element, in its non-fault position, bears against an edge of the strip/strip component or a face of the strip/strip component.

11. The inhaler of claim 4, wherein the element is in the form of a piston element which has a first end, which bears against an edge of the component of the strip when in the non-fault position, and the blocking member at a second end of the piston element which is spaced from the first end in a first direction, and wherein the piston element is adapted to move in the first direction to the fault indicating position in the absence of the strip component.

12. The inhaler of claim 4, wherein the element is in the form of a lever element which bears against a face of the strip component on a first side thereof in its non-fault indicating position, and wherein the lever element has (i) a hub about which the lever member is rotatably mounted, (ii) the blocking member spaced from the hub, and (iii) a biasing member for biasing the lever element against the first side of the strip component in a first direction and to rotate the lever element in the first direction to the fault indicating position in the absence of the strip component.

13. The inhaler of claim 12, wherein the biasing element is a component part of the lever element.

14. The inhaler of claim 1, wherein the element bears against a cover sheet of the strip.

15. The inhaler of claim 1, wherein the element inhibits or prevents operation of the inhaler when in its fault indicating position.

* * * * *